United States Patent
Miyako et al.

(10) Patent No.: US 12,071,350 B2
(45) Date of Patent: Aug. 27, 2024

(54) MODIFIED CARBON NANOMATERIAL, NANOCLUSTER, SUBSTANCE DELIVERY CARRIER AND PHARMACEUTICAL COMPOSITION

(71) Applicants: NATIONAL INSTITUTE OF ADVANCED INDUSTRIAL SCIENCE AND TECHNOLOGY, Tokyo (JP); DAICEL CORPORATION, Osaka (JP)

(72) Inventors: Eijiro Miyako, Tsukuba (JP); Yue Yu, Tsukuba (JP); Masahiro Nishikawa, Tokyo (JP); Ming Liu, Tokyo (JP); Takahiro Tei, Tokyo (JP)

(73) Assignees: NATIONAL INSTITUTE OF ADVANCED INDUSTRIAL SCIENCE AND TECHNOLOGY, Tokyo (JP); DAICEL CORPORATION, Osaka (JP)

( * ) Notice: Subject to any disclaimer, the term of this patent is extended or adjusted under 35 U.S.C. 154(b) by 153 days.

(21) Appl. No.: 17/437,937

(22) PCT Filed: Mar. 3, 2020

(86) PCT No.: PCT/JP2020/008815
§ 371 (c)(1),
(2) Date: Sep. 10, 2021

(87) PCT Pub. No.: WO2020/184272
PCT Pub. Date: Sep. 17, 2020

(65) Prior Publication Data
US 2022/0169517 A1    Jun. 2, 2022

(30) Foreign Application Priority Data

Mar. 11, 2019 (JP) .................. 2019-044209

(51) Int. Cl.
*C01B 32/28*    (2017.01)
*B82Y 30/00*    (2011.01)
(Continued)

(52) U.S. Cl.
CPC .............. *C01B 32/28* (2017.08); *C01B 32/26* (2017.08); *B82Y 30/00* (2013.01); *B82Y 40/00* (2013.01)

(58) Field of Classification Search
CPC ......... C01B 32/28; C01B 32/26; C01B 32/15; C01B 32/25; B82Y 30/00; B82Y 40/00;
(Continued)

(56) References Cited

U.S. PATENT DOCUMENTS

2010/0261926 A1    10/2010   Komatsu et al.
2018/0289836 A1*   10/2018   Spiller ............... A61K 47/6929
(Continued)

FOREIGN PATENT DOCUMENTS

JP    2010-202458 A    9/2010
JP    2010-248023 A    11/2010
(Continued)

OTHER PUBLICATIONS

Kang, et al., Fabrication of blue-fluorescent nanodiamonds modified with alkyl isocyanate for cellular bioimaging, Colloids and Surfaces B: Biointerfaces 2018; 167: 191-196 (Year: 2018).*
(Continued)

*Primary Examiner* — Daniel C. McCracken
(74) *Attorney, Agent, or Firm* — Birch, Stewart, Kolasch & Birch, LLP

(57) ABSTRACT

The present invention provides a nanocluster in which a carbon nanomaterial modified with a higher alkyl group or a higher alkenyl group is self-assembled.

17 Claims, 12 Drawing Sheets

(51) Int. Cl.
*B82Y 40/00* (2011.01)
*C01B 32/26* (2017.01)

(58) Field of Classification Search
CPC ........ B82Y 5/00; A61K 9/0019; A61K 9/143; A61K 9/146; A61K 47/10; A61K 9/51; A61K 9/5115
See application file for complete search history.

(56) References Cited

U.S. PATENT DOCUMENTS

| | | | |
|---|---|---|---|
| 2020/0123012 | A1 | 4/2020 | Makino et al. |
| 2020/0384111 | A1 | 12/2020 | Miyako et al. |

FOREIGN PATENT DOCUMENTS

| | | | |
|---|---|---|---|
| JP | 2017-186234 A | 10/2017 | |
| JP | 2017-186235 A | 10/2017 | |
| WO | WO 2019/116936 A1 | 6/2019 | |

OTHER PUBLICATIONS

Lu, et al., PEG Grafted-Nanodiamonds for the Delivery of Gemcitabine, Macromol. Rapid Commun. 2016; 37: 2023-2029 (Year: 2016).*

Shalaginov, et al., Characterization of nanodiamonds for metamaterial applicaiotns, Appl. Phys. B 2011; 105: 191-195 (Year: 2011).*

Tinwala, et al., Production, surface modification and biomedical applications of nanodiamonds: A sparkling tool for theranostics, Materials Science & Engineering C 2019; 97: 913-931 (Year: 2019).*

Octadecylamine, accessed online at https://pubchem.ncbi.nlm.nih.gov/compound/Octadecylamine on Dec. 11, 2023 (Year: 2023).*

Guan et al., "Nanodiamond as the pH-Responsive Vehicle for an Anticancer Drug," Small, 2010, vol. 6, No. 14, pp. 1514-1519.

International Preliminary Report on Patentability and English translation of the Written Opinion of the International Searching Authority for International Application No. PCT/JP2020/008815, dated Sep. 23, 2021.

International Search Report for International Application No. PCT/JP2020/008815, dated May 26, 2020, with an English translation.

Kang et al., "Fabrication of blue-fluorescent nanodiamonds modified with alkyl isocyanate for cellular bioimaging," Colloids and Surfaces B: Biointerfaces, 2018, vol. 167, pp. 191-196.

Moore et al., "Diamond-Lipid Hybrids Enhance Chemotherapeutic Tolerance and Mediate Tumor Regression," Adv. Mater., 2013, vol. 25, pp. 3532-3541.

Nakanishi et al., "Flower-Shaped Supramolecular Assemblies: Hierarchical Organization of a Fullerene Bearing Long Aliphatic Chains," Small, 2007, vol. 3, No. 12, pp. 2019-2023.

Yu et al., "Amphipathic Nanodiamond Supraparticles for Anticancer Drug Loading and Delivery," ACS Appl. Mater. Interfaces, 2019, vol. 11, pp. 18978-18987.

Yu et al., "Anticancer drug delivery to cancer cells using alkyl amine-functionalized nanodiamond supraparticles," Nanoscale Advances, 2019, vol. 1, No. 9, pp. 3406-3412.

* cited by examiner

MODIFIED CARBON NANOMATERIAL, NANOCLUSTER, SUBSTANCE DELIVERY CARRIER AND PHARMACEUTICAL COMPOSITION

TECHNICAL FIELD

The present invention relates to a modified carbon nanomaterial, a nanocluster, a substance delivery carrier and a pharmaceutical composition.

In the present specification, the following abbreviations are used.
- NDc: carboxylated nanodiamond
- ND: nanodiamond
- NDc-ori: unmodified carboxylated nanodiamond raw material
- SP: super particle
- NDc-SP: nanocluster of carboxylated nanodiamonds modified with an alkyl group
- PEG: polyethylene glycol
- PEGMEM: polyethylene glycol methyl ether methacrylate
- DSPE: distearoylphosphatidylethanolamine
- F127: Pluronic F-127
- CPT: camptothecin
- PTX: paclitaxel

BACKGROUND ART

In addition to the inherent properties of diamonds, carbon nanodiamonds (referred to hereinafter as "CND") also exhibit characteristics including a small average particle diameter and a large specific surface area, and provide merits such as being relatively inexpensive and easy to obtain. CND can be manufactured by methods such as an explosion method or a high-temperature/high-pressure method (Patent Document 1). CND also exhibit low toxicity, superior biocompatibility, and stable fluorescence properties, and therefore applications in the biomedical field are being widely studied. Furthermore, Patent Documents 2 and 3 disclose modified CND and methods for manufacturing the same.

As an example of an application of CND in the biomedical field, Non-Patent Literature 1 indicates that a cisplatin-CND complex is produced by causing CND to carry cisplatin, which is an anticancer drug, and indicates that if the pH is in the acidic range, the cisplatin can be released from the complex, and that the drug released from the complex retains the same level of cytotoxicity as that of the free cisplatin. Furthermore, Non-Patent Literature 2 reports that the anticancer drug epirubicin is adsorbed on a CND surface through hydrophobic interaction, and solubility is increased by wrapping the epirubicin-CND complex with a lipid vesicle to which an antibody (anti-EGRF-PEG) specific to the epidermal growth factor receptor (EGFR) of colon cancer is bound. Non-Patent Literature 2 also describes the drug accumulation effect and efficacy on cancer cells.

Basic problems with typical complexes that carry a drug on CND include a low amount of drug that is carried, and a significant reduction in the dispersibility in water after formation of the complex.

In order to improve the solubility, dispersibility, and dispersion stability of CND in both water and polar organic solvents, modifying the surface of the CND with a polymer has been proposed. For example, Patent Document 4 indicates that the solubility, dispersibility, and dispersion stability of nanodiamonds in water and polar organic solvents are greatly improved by modifying the surface of the nanodiamonds with a specific group containing a polyglycerin chain. However, in the prior art, main focus was basically placed on increasing the dispersibility of the CND, and there has been almost no evaluations pertaining to self-assembling capabilities using CND after surface chemical modification and almost no research pertaining to nanostructure control for the purpose of carrying a drug.

CITATION LIST

Patent Document

Patent Document 1: JP 2010-202458 A
Patent Document 2: JP 2017-186234 A
Patent Document 3: JP 2017-186235 A
Patent Document 4: JP 2010-248023 A

Non-Patent Literature

Non-Patent Literature 1: Bo Guan et al., Small 2010, 6, 1514-1519
Non-Patent Literature 2: Laura Moore et al., Adv. Mater. 2013, 25, 3532-3541

SUMMARY OF INVENTION

Technical Problem

A main object of the present invention is to provide a material that can effectively carry a physiologically active substance such as a pharmaceutical product or perfume, and also exhibits excellent solubility in a physiological environment.

Solution to Problem

The present invention provides the following modified carbon nanomaterial, nanocluster, substance delivery carrier, and pharmaceutical composition.

1. A nanocluster in which a carbon nanomaterial modified with a higher alkyl group or a higher alkenyl group is self-assembled.
2. The nanocluster according to 1, wherein the carbon nanomaterial is further modified with a polyalkylene glycol.
3. The nanocluster according to 2, modified with polyethylene glycol.
4. The nanocluster according to any one of 1 to 3, wherein the higher alkyl group or the higher alkenyl group, and the polyalkylene glycol are linked to the carbon nanomaterial by any linking group selected from the group consisting of —NH—, —O—, —CO—O—, —O—CO—, —CO—NH—, —NH—CO—, —NH—CO—O—, —O—CO—NH—, —O—CO—O—, and —NH—CO—NH—.
5. The nanocluster according to any one of 1 to 4, wherein the carbon nanomaterial has at least one surface group selected from the group consisting of OH, COOH, and $NH_2$, and the higher alkyl group or higher alkenyl group is bonded to the carbon nanomaterial through the surface group.
6. The nanocluster according to 2, wherein the carbon nanomaterial has at least one surface group selected from the group consisting of OH, COOH, and $NH_2$, and the polyalkylene glycol is bonded to the carbon nanomaterial through the surface group.

7. The nanocluster according to any one of 1 to 5, complexed with an active ingredient.
8. The nanocluster according to 7, wherein the active ingredient is a physiologically active substance, a labeling substance, a perfume, an essential oil, or an organic pigment.
9. The nanocluster according to any one of 1 to 8, wherein the carbon nanomaterial is a carbon nanodiamond or carbon nanodots.
10. A delivery carrier for an active ingredient, the delivery carrier containing the nanocluster described in any one of 1 to 9.
11. A carbon nanomaterial modified with a higher alkyl group and/or a higher alkenyl group, and a polyalkylene glycol.
12. The carbon nanomaterial according to 11, wherein the higher alkyl group or higher alkenyl group, and the polyalkylene glycol are linked by any linking group selected from the group consisting of —NH—, —O—, —CO—O—, —O—CO—, —CO—NH—, —NH—CO—, —NH—CO—O—, —O—CO—NH—, —O—CO—O—, and —NH—CO—NH—.
13. The carbon nanomaterial according to 11 or 12, wherein the carbon nanomaterial is a carbon nanodiamond.
14. A pharmaceutical composition containing the self-assembled nanocluster described in 1, the self-assembled nanocluster being complexed with a drug.

Advantageous Effects of Invention

According to the present invention, a surface-chemically modified carbon nanomaterial cluster that is capable of effectively carrying an active ingredient such as a physiologically active substance, a perfume, or an organic pigment and that demonstrates excellent solubility in a physiological environment, and a composite material such as a pharmaceutical composition containing the nanocluster can be provided.

BRIEF DESCRIPTION OF DRAWINGS

FIG. 2($b$) is a graph showing the results of particle diameters obtained through DLS measurements of the various NDc-SP. It was found that the particle diameter increases depending on the chain length of the alkyl chain. It is thought that this occurs because interaction between NDc particles increases due to the increase in the hydrophobicity of the NDc surface when the chain length is increased, and as a result, particles with a large diameter are formed. FIG. 2($c$) is TEM images of various NDc-SP. A highly magnified image is displayed in the upper left of each TEM image. From these images, it is clear that similar to the results of dynamic light scattering (DLS), the actual particle diameter also increases as the alkyl chain length becomes longer. Oct(C8) and Oct(C8)-NDc-SP indicate nanoclusters in which octyl group-modified NDc are self-assembled, Dod(C12) and Dod(C12)-NDc-SP indicate nanoclusters in which dodecyl group-modified NDc are self-assembled, and Ole(C18) and Ole(C18)-NDc-SP indicate nanoclusters in which oleyl group-modified NDc are self-assembled.

FIG. 3($b$) is a graph showing thermogravimetric analysis (TGA) measurement results of NDc-ori and various NDc-SP. From these measurement results, it was found that the percentages of Oct (C8), Dod (C12), and Ole (C18) clusters in the NDc-SP were approximately 13% w/w, approximately 17% w/w, and approximately 35% w/w, respectively.

FIG. 4($b$) is a graph showing the UV-Vis-NIR absorption spectra before and after camptothecin (CPT) encapsulation in Dod(C12)-NDc-SP. Clear peaks originating from CPT can be confirmed after CPT encapsulation, suggesting that CPT has been successfully introduced to the NDc-SP.

FIG. 4($c$) is a graph showing the anti-cancer activity of CPT@NDc-ori, CPT@Oct(C8)-NDc-SP, and CPT@Dod(C12)-NDc-SP. The graph shows the cell viability after 24 hours of exposure of various nanocomplexes using human U2OS cells. CPT@Dod(C12)-NDc-SP was found to have 10% higher anti-cancer activity compared to the other nanocomplexes. It is thought that the affinity to cancer cells is further increased by the long alkyl chains derived from Dod (C12), and thereby higher anti-cancer activity is exhibited. FIG. 4($d$) is a graph showing the results of comparison testing of anti-cancer activity after 24 hours of exposure to U2OS of general nanomedicines (PEGMEM, F127, DSPE-PEG) to which CPT was introduced and CPT@Dod(C12)-NDc-SP. When CPT@Dod(C12)-NDc-SP was used, approximately 90% of the cancer cells were killed. This result showed an improvement in pharmacological activity of up to 57% compared to PEGMEM (killed approximately 34% of cancer cells), F127 (killed approximately 33% of cancer cells), and DSPE-PEG (killed approximately 46% of cancer cells). The above results strongly suggest that NDc-SP is useful as a nanocarrier for anti-cancer drugs.

FIG. 6($b$) is a graph showing the particle diameters according to DLS measurements of NDa-ori and various NDa-SPs. It was found that the particle diameter can be controlled according to the alkyl chain length. FIG. 6($c$) is TEM images of various NDa-SPs. It is clear that the particle diameter increases depending on the alkyl chain length, but complements the DLS results. FIG. 6($d$) is high magnification TEM images of NDa-ori and various NDa-SP. NaOc(C8)-NDa-SP indicates nanoclusters in which octyl group-modified NDa are self-assembled, NaLA(C12)-NDa-SP indicates nanoclusters in which dodecyl group-modified NDa are self-assembled, and NaOle(C18)-NDa-SP indicates nanoclusters in which oleyl group-modified NDa are self-assembled.

FIG. 12(a) is an evaluation of the cytotoxicity of 050GS-NaOc(C8)-NDa-SP (left) and 8Arm-NaLA(C12)-NDa-SP (right) after 24 hours of exposure to SKOV3, U2OS, and TIG3. FIG. 12(b) are graphs showing the results of anti-cancer activity comparative testing of PTX@050GS-NaOc(C8)-NDa-SP, PTX@8Arm-NaLA(C12)-NDa-SP and the PTX formulation Abraxane approved by the FDA. The various nanocomplexes were examined at 24 hours after exposure (left) and at 48 hours after exposure (right) using SKOV3 cells. FIG. 12(c) presents phase difference images (Phase) and crystal violet staining (CV staining) images of SKOV3 cells exposed to various nanocomplexes for 24 hours. The ND concentration in the 050GS-NaOc(C8)-NDa-SP and 8Arm-NaLA(C12)-NDa-SP was 30 μg ml$^{-1}$. The concentrations of PTX and ND in the PTX@050GS-NaOc(C8)-NDa-SP and PTX@8Arm-NaLA(C12)-NDa-SP were 10 ng ml$^{-1}$ and 30 ng ml$^{-1}$, respectively. From the images, it is found that the anti-cancer activity of PTX@050GS-NaOc(C8)-NDa-SP and PTX@8Arm-NaLA(C12)-NDa-SP is clearly high.

DESCRIPTION OF EMBODIMENTS

Figure 1:
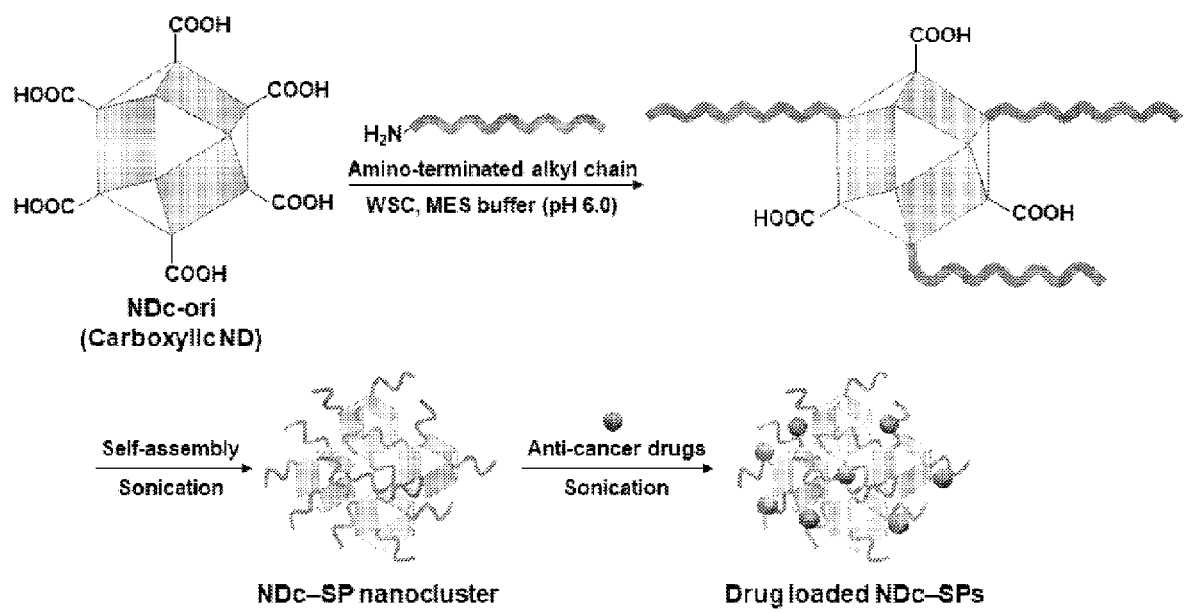
FIG. 1 illustrates a method for synthesizing super particles (SP) (NDc-SP) using nanodiamonds (NDc) having a carboxyl group. Self-assembled NDc-SP nanoclusters can be prepared by covalently bonding the carboxyl groups of NDc-ori (raw material composed of NDc) and the amino groups of amino-terminated alkyl molecules through a condensation reaction and subjecting to sonication.

In the present specification, carbon nanomaterials include carbon nanodiamonds and carbon nanodots.

The carbon nanomaterials used in the production of nanoclusters are modified with a higher alkyl group or a higher alkenyl group. Carbon nanomaterials modified with these functional groups may be described as "modified carbon nanomaterials."

The modified carbon nanomaterial according to an embodiment of the present invention contains a higher alkyl group or higher alkenyl group at an approximate amount of from 0.0001 to 30 mass %, preferably from 0.001 to 20 mass %, preferably from 0.01 to 15 mass %, and preferably from 0.05 to 10 mass %.

The higher alkyl group or higher alkenyl group is linked to the carbon nanomaterial by a divalent linking group. Examples of the divalent linking group include —NH—, —O—, —CO—O—, —O—CO—, —CO—NH—, —NH—CO—, —NH—CO—O—, —O—CO—NH—, —O—CO—O—, and —NH—CO—NH—.

Examples of the higher alkyl group include linear or branched $C_6$-$C_{24}$ alkyl groups, such as hexyl, heptyl, octyl, nonyl, decyl, undecyl, dodecyl, tridecyl, tetradecyl, pentadecyl, hexadecyl, isohexadecyl, heptadecyl, octadecyl, isooctadecyl, nonadecyl, icosyl, henicosyl, docosyl, tricosyl, and tetracosyl. The higher alkyl group is preferably a $C_8$-$C_{18}$ alkyl group, more preferably a $C_5$-$C14$ alkyl group, and even more preferably a $C_{10}$-$C_{14}$ alkyl group.

Examples of the higher alkenyl group include linear or branched $C_6$-$C_{24}$ alkenyl groups, such as hexenyl, heptenyl, octenyl, nonenyl, decenyl, undecenyl, dodecenyl, tridecenyl, tetradecenyl, pentadecenyl, hexadecenyl (palmitoleyl), isohexadecenyl, heptadecenyl, octadecenyl (oleyl, Ole), isooctadecenyl, nonadecenyl, icocenyl, henicocenyl, dococenyl, tricocenyl, and tetracocenyl. The higher alkenyl group is preferably a $C_8$-$C_{18}$ alkenyl group, more preferably a $C_{12}$-$C_{18}$ alkenyl group, and more preferably a $C_{14}$-$C_{18}$ alkenyl group.

The carbon nanomaterials used in the production of the nanoclusters according to an embodiment of the present invention may be further modified with a polyalkylene glycol. Examples of the polyalkylene glycol include polyethylene glycol, polypropylene glycol, polybutylene glycol, and polyethylene glycol-polypropylene glycol copolymers.

The average particle diameter of the primary particles of the carbon nanomaterial prior to modification with a higher alkyl group and/or a higher alkenyl group and a polyalkylene glycol is preferably 10 nm or less, and more preferably from 1 to 10 nm.

The average particle diameter of the primary particles of the carbon nanomaterial modified with a higher alkyl group and/or a higher alkenyl group and a polyalkylene glycol is preferably 12 nm or less, more preferably from 1 to 12 nm, and even more preferably from 3 to 12 nm.

The average particle diameter of the primary particles of the carbon nanomaterial before or after modification may be measured through dynamic light scattering, and may be determined by small-angle X-ray scattering measurements (SAXS method) using an X-ray diffraction apparatus (trade name "SmartLab", available from Rigaku Corporation).

As the carbon nanomaterial used in the production of nanoclusters according to an embodiment of the present invention, a carbon nanomaterial (hereinafter, also referred to as "CNM") having a large number of functional groups such as OH, COOH, and $NH_2$ on the surface is preferably used. Carbon nanomaterials having a large number of groups such as OH, COOH, and $NH_2$ on the surface are known, and carbon nanomaterials modified with a higher alkyl group or a higher alkenyl group can be obtained according to Schemes (1) to (10) below using such materials.

Schemes

[Chem. 1]

(1)

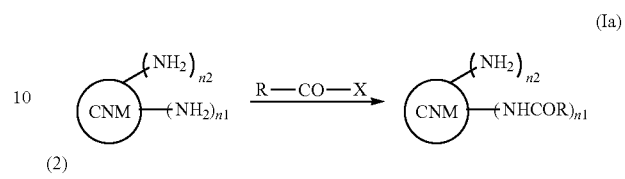

(2)

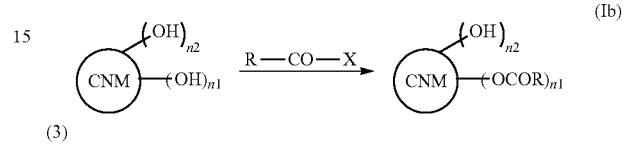

(3)

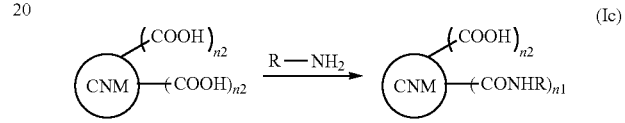

(4)

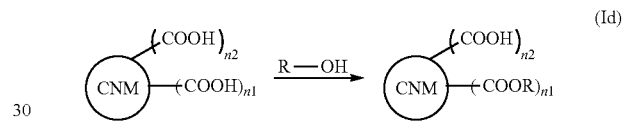

(5)

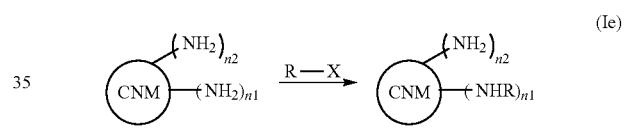

(6)

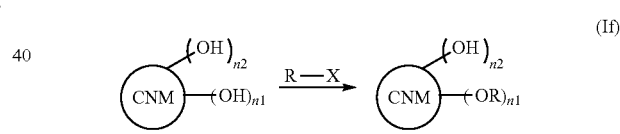

[Chem. 2]

(7)

(8)

(9)

(10)

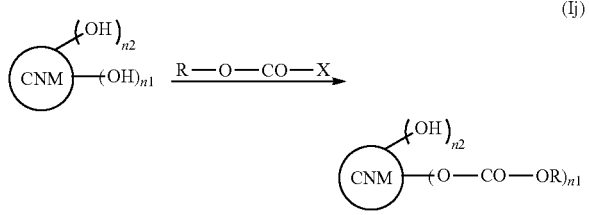

(In these schemes, X denotes Cl, Br, or I. CNM denotes a carbon nanomaterial; n1 is an integer of 1 or greater; n2 is an integer of 0 or greater; and R denotes a higher alkyl group or higher alkenyl group.)

The reactions in Schemes (1) through (10) above can be carried out according to a conventional method. A targeted product can be obtained by using from 1 mg to an excess amount of any compound selected from R—COX, R—NH$_2$, R—OH, and R—X with respect to 1 g of a carbon nanomaterial having a surface group of OH, NH$_2$, or COOH, and carrying out a reaction for 1 to 24 hours at a temperature of from 0° C. to the boiling temperature of the solvent. Examples of the solvent include halogenated hydrocarbons such as chloroform, methylene chloride, and 1,2-dichloroethane; aromatic hydrocarbons such as toluene; tetrahydrofuran, diethyl ether, and diisopropyl ether.

Compounds (Ia) to (Ij) obtained in Schemes (1) through (10) described above can be further modified with a polyalkylene glycol by reacting each of the unreacted functional groups (OH, COOH, NH$_2$) with a polyalkylene glycolizing reagent (R$^2$—Y$^2$—X$^2$; wherein R$^2$ denotes a group containing a polyalkylene glycol moiety, Y$^2$ denotes a single bond or a divalent spacer group, and X$^2$ denotes NH$_2$, OH, COOH, or N-hydroxysuccinimide). Examples of the divalent spacer group include methylene, ethylene, propylene, butylene, (1,2-, 1,3-, 1,4-)phenylene, —CH$_2$CH$_2$O—, —CH$_2$CH$_2$CH$_2$O—, —CH$_2$CH$_2$CH$_2$CH$_2$O—, —CH$_2$CH$_2$NH—, —CH$_2$CH$_2$CH$_2$NH—, —CH$_2$CH$_2$CH$_2$CH$_2$NH—, —CH$_2$CH$_2$CONH—, —CH$_2$CH$_2$CH$_2$CONH—, —CH$_2$CH$_2$CH$_2$CH$_2$CONH—, —CH$_2$CH$_2$NHCO—, —CH$_2$CH$_2$CH$_2$NHCO—, —CH$_2$CH$_2$CH$_2$CH$_2$NHCO—, —CH$_2$CH$_2$CO—, —CH$_2$CH$_2$CH$_2$CO—, —CH$_2$CH$_2$CH$_2$CO—, —CH$_2$CH$_2$COO—, —CH$_2$CH$_2$CH$_2$COO—, —CH$_2$CH$_2$CH$_2$CH$_2$COO—, —CH$_2$CH$_2$OCO—, —CH$_2$CH$_2$CH$_2$OCO—, and —CH$_2$CH$_2$CH$_2$CH$_2$OCO—. A single divalent spacer group may be used alone, or two or more divalent spacer groups may be combined and used. The reaction to introduce the polyalkylene glycol is carried out for 1 to 24 hours at a temperature of from 0° C. to the boiling temperature of the solvent using a polyalkylene glycolating reagent in an amount of from 100 mg to excess relative to 1 g of the compounds (Ia) to (Ij), and thereby a targeted carbon nanomaterial modified with a higher alkyl group and/or higher alkenyl group and a polyalkylene glycol can be obtained. Examples of the solvent include halogenated hydrocarbons such as chloroform, methylene chloride, and 1,2-dichloroethane; aromatic hydrocarbons such as toluene; tetrahydrofuran, diethyl ether, and diisopropyl ether.

The nanoclusters according to an embodiment of the present invention can be produced by suspending a carbon nanomaterial modified with a higher alkyl group and/or higher alkenyl group, and, if necessary, a polyalkylene glycol group, in a suitable aqueous medium such as water or a buffer solution, and self-assembling through sonication. After sonication, the self-assembled nanoclusters can be separated by removing, through a purification operation such as centrifugation, unreacted functional group-modified carbon nanomaterials that do not form clusters.

The nanoclusters according to an embodiment of the present invention can be complexed with an active ingredient by being suspended in a suitable solvent containing the active ingredient. The active ingredient is present within or on the surface of the nanoclusters. Examples of the active ingredient include physiologically active substances, labeling substances, essential oils, perfumes, and organic pigments.

Examples of labeling substances include fluoresceins such as fluorescein, Oregon green, eosin, and erythrosine; rhodamines such as tetramethyl rhodamine derivatives, Texas red derivatives, rhodamine B base, lissamine rhodamine B, and rhodamine 6G; coumarins; dansyl-type (dimethylaminonaphthalene sulfonic acid type) fluorescent pigments; NBD-type pigments; pyrene; phycobiliproteins such as R-phycoerythrin, phlophycocyanin and allophycocyanin; BODIPY derivatives; Cy (trade name) pigments such as Cy3, Cy3.5, Cy5, and Cy5.5; and Alexa (trade name) fluor dyes such as Alexa Fluor 350, 405, 430, 488, 532, 546, 555, 568, 594, 633, 647, 680, 700, and 750. A single labeling substance may be used alone, or two or morelabeling substances may be used in combination.

Examples of the essential oils include sweet orange, bitter orange, petitgrain, lemon, grapefruit, lime, bergamot, mandarin, neroli, peppermint, spearmint, lavender, chamomile, rosemary, eucalyptus, sage, basil, rose, geranium, jasmine, ylang-ylang, anise, fennel, star anise, clove, cinnamon, ginger, nutmeg, cardamom, hops, cedar, cypress, vetiver, patchouli, and labdanum. One or more essential oils may be used.

Examples of the perfume component include monoterpenes, such as 1-menthol, α-pinene, Jβ-pinene, myrcene, camphene, and limonene; sesquiterpenes, such as valencene, cedrene, caryophyllene, and longifolene; 1,3,5-undecatriene, butanol, pentanol, isoamyl alcohol, hexanol, prenol, (Z)-3-hexen-1-ol, 2,6-nonadienol, linalool, geraniol, citronellol, tetrahydromyrcenol, farnesol, nerolidol, cedrol, benzyl alcohol, phenylethyl alcohol, furfuryl alcohol, acetaldehyde, isovaleraldehyde, hexanal, octanal, nonanal, decanal, (E)-2-hexenal, 2,4-octadienal, citronellal, citral, benzaldehyde, cinnamaldehyde, vanillin, ethyl vanillin, furfural, heliotropin, 2-heptanone, 2-undecanone, 1-octen-3-one, acetoin, diacetyl, 2,3-pentanedione, maltol, ethyl maltol, 2,5-dimethyl-4-hydroxy-3(2H)-furanone, hydroxyketone, carvone, menthone, nootkatone, and other such terpene ketones, α-ionone, β-ionone, β-damascenone, raspberry ketone, rose oxide, linalool oxide, menthofuran, theaspirane, methyl chavicol, anethole, ethyl acetate, isoamyl acetate, linalyl acetate, geranyl acetate, lavandulyl acetate, ethyl butyrate, ethyl caproate, benzyl acetate, methyl salicylate, γ-decalactone, γ-dodecalactone, δ-decalactone, δ-dodecalactone, 7-decen-4-olide, 2-decen-5-olide, butyric acid, 4-methyl-3-pentenoic acid, octanoic acid, stearic acid, oleic acid, linoleic acid, linolenic acid, indole, skatole, pyridine, alkyl-substituted pyrazine, methyl anthranilate, methanethiol, furfuryl mercaptan, dimethylsulfide, dimethyl disulfide, difurfuryl disulfide, and allyl isothiocyanate. Two or more of these perfume components may be combined and used.

Examples of the organic pigment include annato pigment, cochineal pigment, monascus pigment, β-carotene, hibiscus pigment, saffron yellow, cacao pigments, riboflavin, chlorophyll, caramel, annatto, carmine, laccaic acid, brazilin, crocin, shikonin, shisonin, and rutin.

A nanocluster according to an embodiment of the present invention complexed with an active ingredient gradually releases the active ingredient when administered within or applied to the living body or skin of a mammal (such as a human, mouse, rat, hamster, horse, cow, pig, goat, sheep, rabbit, dog, or cat). Thus, nanoclusters according to an embodiment of the present invention complexed with an active ingredient are useful as pharmaceutical products or pharmaceutical compositions, cosmetic products, and oral compositions. Examples of cosmetic products include foundations, face powders, lotions, emulsions, lipsticks, toners, beauty serums, massage creams, moisturizers, packs, facial cleansers, shampoos, rinses, hair growth agents, and body powders. Examples of oral compositions include mouthwashes, mouth rinses, toothpastes, tooth polishing powders, chewing gums, candy, gummies, and ramune tablets. Examples of dosage forms of pharmaceutical products include tablets, capsules, lozenges, pills, chewable tablets, injectable agents, suppositories, syrups, ointments, and plaster agents. The nanoclusters according to an embodiment of the present invention gradually release the active ingredient, and thus are also useful as delivery carriers of active ingredients.

Physiologically active substances include drugs, nucleic acids, and proteins. Examples of drugs include, but are not limited to, anti-tumor agents, anti-hypertension agents, anti-hypotensive agents, anti-psychotic agents, analgesics, anti-depressants, antimanic agents, anti-anxiety agents, sedatives, hypnotics, anti-epileptic agents, opioid agonists, asthma therapeutics, anesthetics, anti-arrhythmia agents, arthritis therapeutic agents, anti-spasmodic agents, ACE inhibitors, decongestants, antibiotics, anti-angina agents, diuretics, anti-Parkinson's disease agents, bronchodilators, antidiuretics, diuretics, anti-hyperlipidemia agents, immunosuppressive agents, immunomodulatory agents, anti-emetics, anti-infective agents, anti-neoplastic agents, anti-fungal agents, antiviral agents, anti-diabetic agents, anti-allergenic agents, antipyretics, gout suppressants, antihistamines, anti-pruritic agents, bone regulators, cardio-vascular agents, cholesterol lowering agents, antimalarials, antitussives, expectorants, mucolytic agents, nasal packing agents, dopamine agonists, gastrointestinal agents, muscle relaxants, neuromuscular blockers, parasympathomimetic agents, prostaglandins, stimulants, appetite suppressers, thyroid or anti-thyroid agents, hormones, anti-migraine agents, anti-obesity agents, and anti-inflammatory agents. A preferred drug is an anti-tumor agent. Examples of anti-tumor agents include hormonal therapeutic agents (e.g., fosfestrol, diethylstilbestrol, chlorotrianiseline, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testolactone, aminoglutethimide, LH-RH agonists (e.g., goserelin acetate, buserelin, leuprorelin), droloxifene, epitiostanol, ethynyl estradiol sulfonate, aromatase inhibitors (e.g., fadrozole hydrochloride, anastrozole, letrozole, exemestane, borazole, formestane), anti-androgens (e.g., flutamide, bicalutamide, nilutamide), 5α-reductase inhibitors (e.g., finasteride, episteride), corticosteroids (e.g., dexamethasone, prednisolone, betamethasone, triamcinolone), androgen synthesis inhibitors (e.g., abiraterone), and retinoids and agents that slow the metabolism of retinoids (e.g., liarozole), and among these, LH-RH agonists (e.g., goserelin acetate, buserelin, leuprorelin)), alkylating agents (e.g., nitrogen mustards, nitrogen mustard-N-oxide hydrochloride, chlorambutyl, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylene melamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulfan, trofosfamide, zinostatin stimalamer, carboquone, adozelesin, cystemustine, bizelesin), anti-metabolites (e.g., mercaptopurine, 6-mercaptopurine riboside, thioinosine, methotrexate, enocitabine, cytarabine, cytarabine ocfosfate, ancitabine hydrochloride, 5-FU-based drugs (e.g., fluorouracil, tegafur, UFT, doxifluridine, carmofur, gallocitabine, and emitefur), aminopterin, leucovorin calcium, tabloid, butocine, calcium folinate, calcium levofolinate, cladribine, emitefur, fludarabine, gemcitabine, hydroxycarbamide, pentostatin, piritrexim, idoxuridine, mitoguazone, tiazofurin, and ambamustine), anti-cancer antibiotics (e.g., actinomycin D, actinomycin C, mitomycin C, chromomycin A3, bleomycin hydrochloride, bleomycin sulfate, pepromycin sulfate, daunorubicin hydrochloride, doxorubicin hydrochloride, aclarubicin hydrochloride, pirarubicin hydrochloride, epirubicin hydrochloride, neocarzinostatin, misramycin, sarkomycin, carzinophilin, mitotane, xorubicin hydrochloride, mitoxantrone hydrochloride, and idarubicin hydrochloride), plant-derived anti-cancer agents (e.g., etoposide, etoposide phosphate, vinblastine sulfate, vincristine sulfate, vindesine sulfate, teniposide, paclitaxel, docetaxel, vinorelbine, camptothecin, irinotecan hydrochloride), biological response modifiers (BRM) (e.g., picibanil, Krestin, schizophyllan, lentinan, ubenimex, interferon, interleukin, macrophage colony stimulating factor, granulocyte colony stimulating factor, erythropoietin, lymphotoxin, BCG vaccine, *Corynebacterium parvum*, levamisole, polysaccharide-K, and procodazol), and drugs that inhibit cell growth factors and the action of receptors thereof (e.g., antibody drugs such as trastuzumab (Herceptin (trade name); anti-HER2 antibody), ZD1839 (Iressa), and Gleevec). Examples of the types of cancers targeted by anti-tumor agents include colorectal cancer, liver cancer, kidney cancer, head and neck cancer, esophageal cancer, stomach cancer, biliary cancer, gallbladder/bile duct cancer, pancreatic cancer, lung cancer, breast cancer, ovarian cancer, cervical cancer, uterine cancer, bladder cancer, prostate cancer, testicular tumors, bone and soft tissue sarcomas, leukemia, malignant lymphoma, multiple myeloma, skin cancer, and brain tumors. Preferable examples includes colorectal cancer, stomach cancer, head and neck cancer, lung cancer, breast cancer, pancreatic cancer, biliary cancer, and liver cancer.

The nucleic acids are not particularly limited and may be DNA, RNA, chimeric nucleic acids of DNA and RNA, or hybrids of DNA/RNA. Further, the nucleic acid can be any of 1 to 3 strands, but is preferably single-stranded or double-stranded. The nucleic acid may be another type of nucleotide that is an N-glycoside of a purine or pyrimidine base, or another oligomer having a non-nucleotide skeleton (e.g., a commercially available peptide nucleic acid (PNA), etc.) or other oligomer with a special bond (provided that the oligomer contains a nucleotide having an arrangement that allows pairing of bases or attachment of bases as found in DNA or RNA). The nucleic acid may also be one with a known modification. Examples include labeled nucleic acids known in the relevant technical field, capped nucleic acids, methylated nucleic acids, nucleic acids having one or more natural nucleotides substituted with an analog, nucleic acids subjected to intramolecular nucleotide modifications, for example, those with uncharged bonds (e.g., methylphosphonates, phosphotriesters, phosphoramidates, and carbamates, etc.), nucleic acids having a charged bond or a sulfur-containing bond (e.g., phosphorothioate, and phosphorodithioate, etc.), for example, nucleic acids having a side chain group such as a protein (nuclease, nuclease inhibitor, toxin, antibody, and signal peptide, etc.) or sugars (e.g., monosaccharides, etc.), nucleic acids having an intercalated compound (e.g., acridine and psoralen, etc.), nucleic acids having a chelate compound (e.g., metals, radioactive metals, boron, oxidative metals, etc.), nucleic acids containing an alkylating agent, and nucleic acids with modified bonds (e.g., α-anomeric nucleic acids, etc.). Preferred nucleic acids include RNA such as siRNA.

An siRNA is a double-stranded oligo RNA consisting of a nucleotide sequence of the mRNA or initial transcript of a target gene or a nucleotide sequence homologous to a partial sequence (preferably within the coding region) of the nucleotide sequence thereof (including the intron portion in the case of an initial transcript), and the complementary strand thereof. The length of the portion that is homologous to the target nucleotide and is contained in the siRNA is usually greater than or equal to approximately 18 bases, and for example, the length may be approximately 20 bases (typically, an approximate length of from 21 to 23 bases). However, the length thereof is not particularly limited as long as RNA interference can be caused. Ordinarily, the total length of the siRNA is approximately greater than or equal to 18 bases, and for example, the total length may be approximately 20 bases (typically, an approximate total length of from 21 to 23 bases). However, the total length is not particularly limited as long as RNA interference can be caused.

The relationship between the target nucleotide sequence and the sequence homologous thereto and contained in the siRNA may be a 100% match, or base mutations may be present (within a range of sameness of at least 70%, preferably 80% or higher, more preferably 90% or higher, and most preferably 95% or higher).

The siRNA may have, at the 5' or 3' end, additional bases that consist of no more than 5 bases, and preferably 2 bases, and which do not form a base pair. The additional base may be DNA or RNA, but when DNA is used, the stability of the siRNA can be improved. Examples of sequences of such additional bases include, but are not limited to, ug-3', uu-3', tg-3', tt-3', ggg-3', guuu-3', gttt-3', ttttt-3', and uuuuu-3'.

The siRNA may be for any target gene. The siRNA is preferably one that targets genes for which an enhanced expression is involved in the onset and/or exacerbation of a disease of interest, and more specifically, is one that targets genes for which an antisense nucleic acid to the gene thereof has advanced to a clinical or preclinical stage, or newly known genes.

The siRNA may be used singly, or in a combination of two or more.

Examples of proteins include enzymes, receptors, antibodies, antigens, and cytokines such as interferons and interleukins.

The approximate average particle diameter of the nanocluster according to an embodiment of the present invention is from 1 to 1000 nm, preferably from 3 to 800 nm, more preferably from 5 to 500 nm, even more preferably from 10 to 300 nm, and particularly from 30 to 250 nm.

The approximate zeta potential of the nanocluster is preferably from 5 to 30 mV, and more preferably from 10 to 25 mV.

When the nanoclusters according to an embodiment of the present invention are complexed with an active ingredient, the approximate content of the active ingredient is from 5 to 50 parts by mass, and preferably from 10 to 20 parts by mass, per 100 parts by mass of the nanoclusters.

EXAMPLES

The present invention will be described in detail below based on examples, but the present invention is not limited to these examples.

Example 1

Experimental Method

1. Synthesis of Super Particle Complex Using Carboxylated Nanodiamonds

Figure 2:
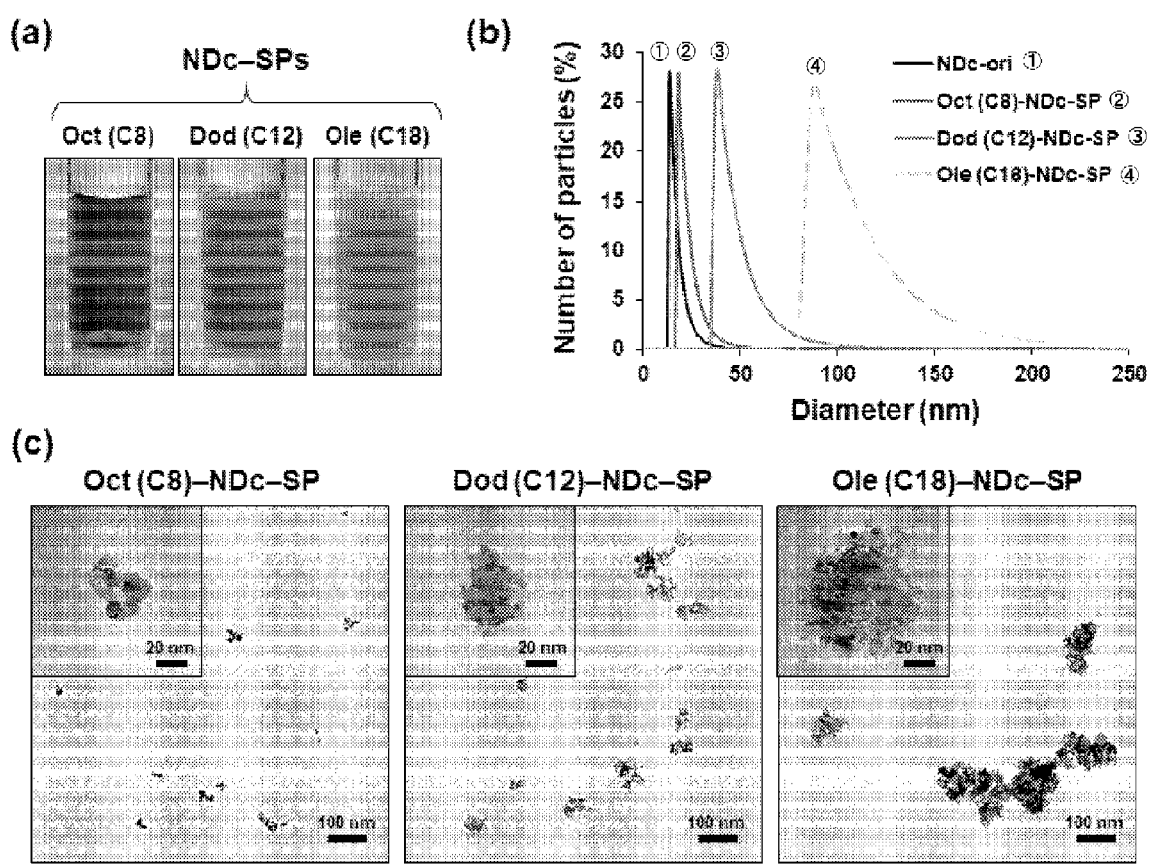
FIG. 2($a$) is a photograph of various NDc-SP aqueous solutions in which amino-terminated alkyl molecules of different alkyl chain lengths (C8-$NH_2$, C12-$NH_2$, C18-$NH_2$) have been introduced. The ND concentration in each case is 5.6 mg $ml^{-1}$.
Figure 3:
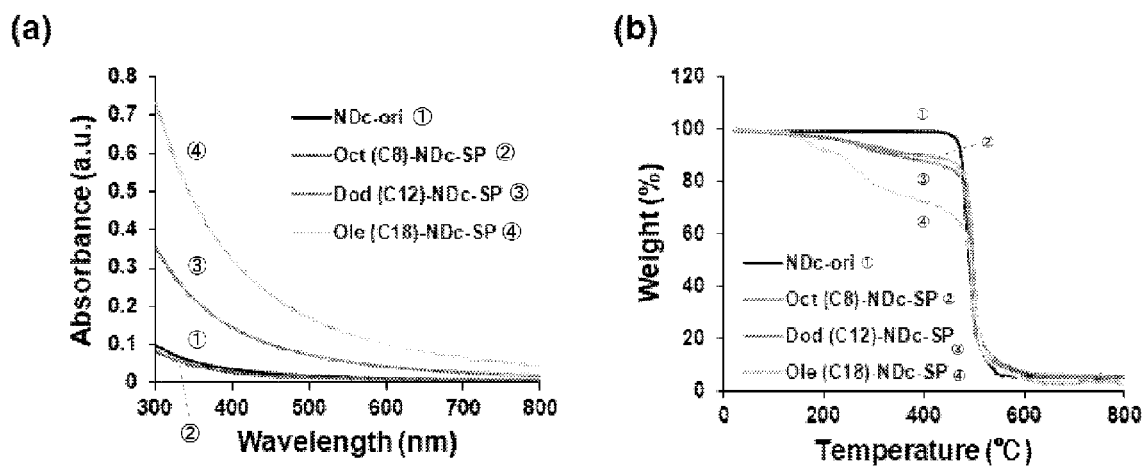
FIG. 3($a$) illustrates the UV-Vis-NIR absorption spectra of various NDc-SP and NDc-ori, which is a raw material for production. The ND concentration is uniformly adjusted to 56 µg $ml^{-1}$.

Carboxylated nanodiamonds (NDc) (particle diameter: from 4 to 5 nm) were prepared by a detonation method according to the disclosure of JP 2017-202940 A or JP 2016-113333 A. The synthesized NDc were purified by nitric acid and fired in a hydrogen gas atmosphere. The elements of the NDc were analyzed using an organic element analyzer (Micro Corder JM10; J-Science Lab Co., Ltd, Kyoto, Japan), and the NDc were found to contain C (86.92%), H (0.44%), and N (2.29%). The purified NDc were dispersed in distilled water by a bead mill (Sand Grinder LSG-4U; Aimex Co., Ltd, Tokyo, Japan). Next, the NDc dispersed aqueous solution was centrifuged to remove the ND insoluble in water. The resulting supernatant solution (NDc-ori) was used in a subsequent experiment. One milliliter of the NDc-ori dispersed aqueous solution (ND concentration=56 mg ml$^{-1}$), amino-terminated alkyl molecules (50 µl of n-octylamine (Oct (C8)), 50 µl of oleylamine (Ole (C18)), or 10 mg of dodecylamine (Dod (C12)) (each purchased from FUJIFILM Wako Pure Chemical, Osaka, Japan)), and 10 mg of 1-ethyl-3-(3-dimethylaminopropyl) carbodiimide hydrochloride (WSC) (FUJIFILM Wako Pure Chemical) were added to 9 ml of a 2-(N-morpholino) ethanesulfonic acid (MES) buffer solution (pH 6.0, 100 mM), and the mixture was irradiated for 5 minutes using a bus-type sonicator (output=80 W, frequency=40 kHz) (USD-2R; AS ONE, Osaka, Japan). After vigorous stirring using a stirrer at room temperature for 1.5 hours, the mixture was centrifuged and washed three times with Milli-Q water. Next, 10 ml of Milli-Q water was added to the precipitate obtained by centrifugation, and the material was re-dispersed by irradiating with ultrasonic waves for 10 minutes using a pulsed sonicator (VCX-600; Sonics, Danbury, CT, USA). The carboxylated nanodiamond super particle (NDc-SP) dispersion was used in subsequent experiments. Three types of carboxylated nanodiamond superparticle (NDc-SP) dispersions were obtained, namely, Oct(C8)-NDc-SP, Dod (C12)-NDc-SP, and Ole(C18)-NDc-SP, and each of these dispersions formed nanoclusters (FIGS. 2(b), 2(c)). The ND concentration in the final product was confirmed to be approximately 5.6 mg ml$^{-1}$ using an ultraviolet-visible-near infrared spectrometer (V-730 BIO; Jasco, Tokyo, Japan). It was also evident through thermogravimetric analysis (Q 500; TA Instruments, New Castle, DE, USA) that the amounts of Oct (C8), Dod (C12), and Ole (C18) in the NDc-SP (clusters) were approximately 13% w/w, 17% w/w, and 35% w/w, respectively.

Figure 4:
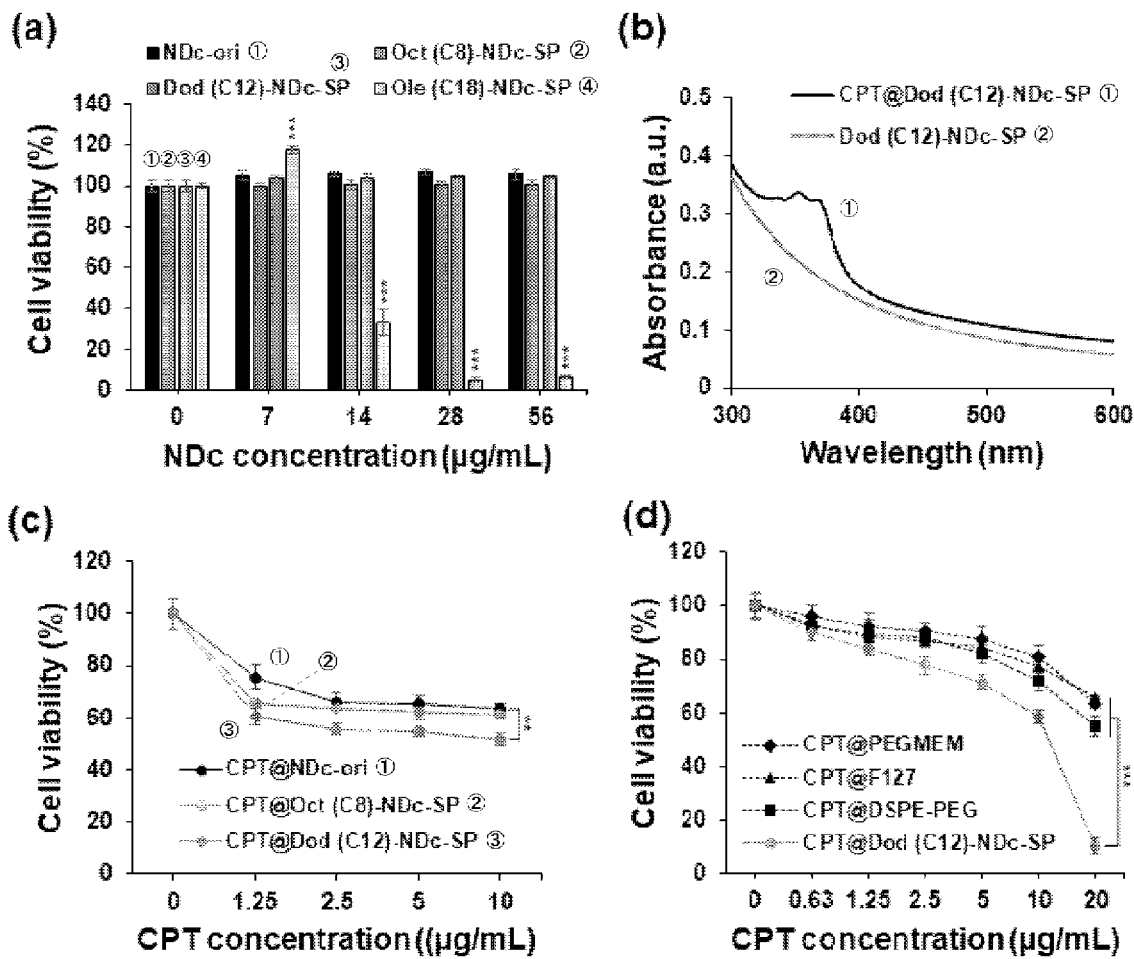
FIG. 4($a$) is a graph showing the results of a cytotoxicity evaluation of various NDc-SP. Viability was measured after 24 hours of exposure of various NDc-SP to human osteosarcoma cells (U2OS).
Figure 5:
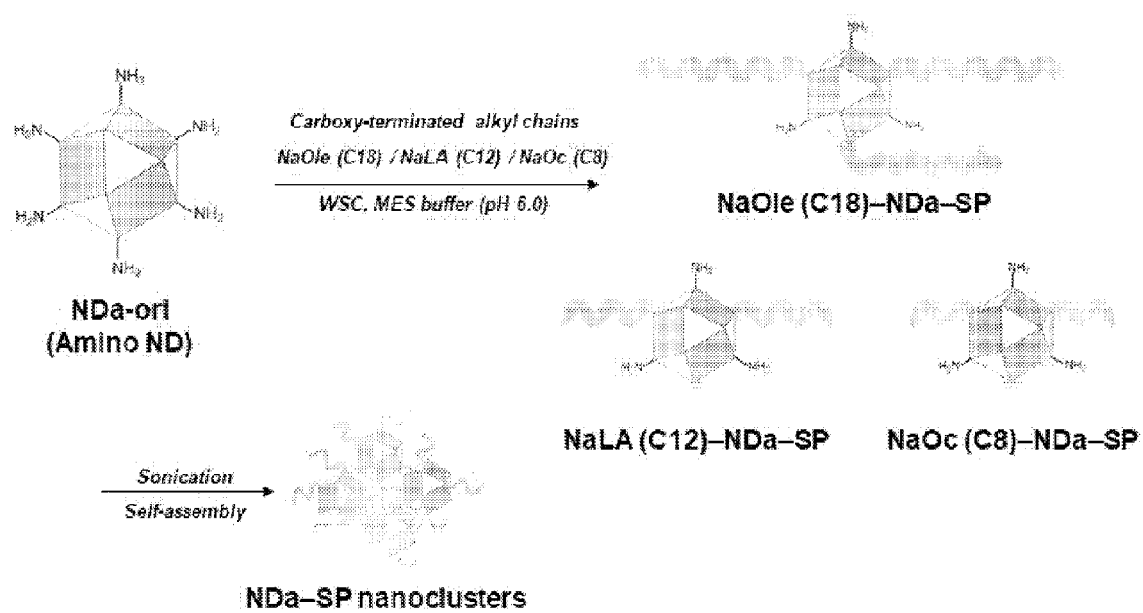
FIG. 5 outlines a method of synthesizing nanoclusters (NDa-SP) using nanodiamonds (NDa) having an amino functional group. Self-assembled NDa-SP nanoclusters can be preprepared by subjecting an amino group of NDa-ori and a carboxyl group of a compound (NaOc (C8), NaLA (C12), NaOle (C18)) having a carboxyl-terminated alkyl chain to a condensation reaction, and thereby covalently bonding with the amino functional group, and then subjecting to sonication.

CPT@Oct(C8)-NDc-SP and CPT@Dod(C12)-NDc-SP complexes were prepared by the following method. Precipitates containing Oct(C8)-NDc-SP or Dod(C12)-NDc-SP washed by centrifugation, and 10 mg of CPT (FUJIFILM Wako Pure Chemical) were mixed in 10 ml of Milli-Q water and then irradiated with pulsed ultrasonic waves for 10 minutes. CPT@NDc-ori was prepared by mixing 10 mg of CPT, 1 ml of an NDc-ori aqueous solution, and 9 ml of Milli-Q water, and then irradiating with pulsed ultrasonic waves for 10 minutes. Both the CPT@Oct(C8)-NDc-SP and the CPT@Dod(C12)-NDc-SP complexes formed nanoclusters (FIGS. 4(b), 4(c), 4(d)). CPT@PEGMEM, CPT@F127, and CPT@DSPE-PEG were prepared by the same method with the exception of using, instead of the ND precipitates, 56 mg of poly(ethylene glycol)methyl ether methacrylate (PEGMEM) (Sigma-Aldrich, St. Louis, MO, USA), 56 mg of pluronic F127 (F127) (FUJIFILM Wako Pure Chemical), or 56 mg of N-(aminopropyl polyethyleneglycol) carbamyl-distearoylphosphatidyl-ethanolamine (DSPE-PEG) (Sunbright DSPE-020PA; Yuka Sangyo, Tokyo, Japan).

2. Synthesis of Super Particle Complex Using Aminated Nanodiamonds

Figure 6:
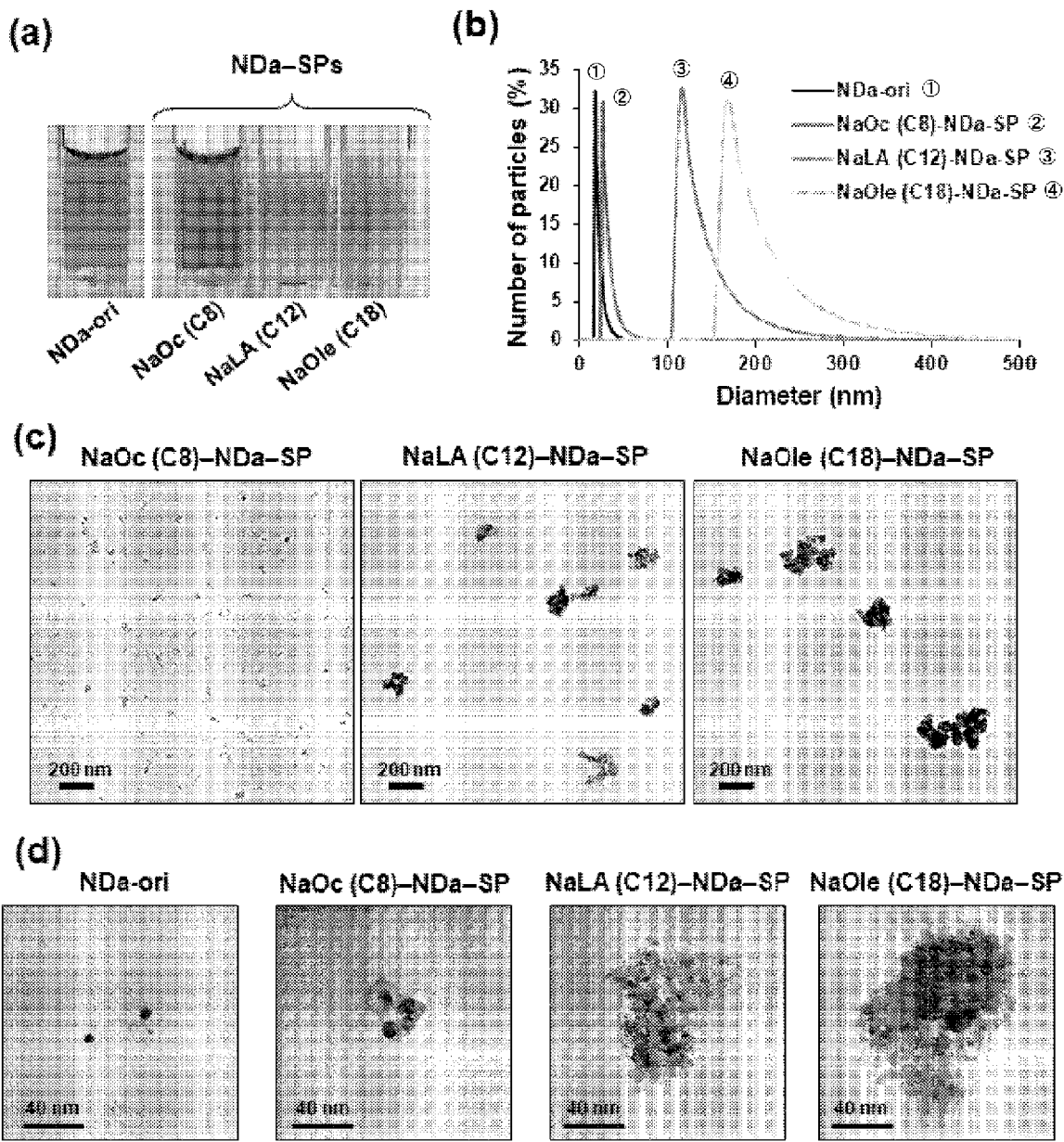
FIG. 6($a$) is a photograph of aqueous solutions of various NDa-SPs (NaOc (C8), NaLA (C12), NaOle (C18)) having an alkyl chain differing from the NDa-ori raw material. The ND concentration in each aqueous solution is 3 mg $ml^{-1}$.

Aminated nanodiamonds (NDa) (particle diameter: from 4 to 5 nm) were synthesized according to previously reported preparation methods (V. V. Danilenko, Combust., Explos. Shock Waves 2005, 41, 577; V. Y. Dolmatov, J. Superhard Mater. 2008, 30, 233; V. Y, Dolmatov, V. Myllymaki and A. Vehanen, J. Superhard Mater. 2013, 35, 143.), The synthesized NDa were purified by nitric acid and fired in a hydrogen gas atmosphere. The elements of the NDa [contents of C (92.20%), H (0.74%), and N (2.30%)] were analyzed using an organic element analyzer (Micro Corder JM10; J-Science Lab Co., Ltd, Kyoto, Japan). The purified NDa were dispersed in distilled water by a bead mill (Sand Grinder LSG-4U; Aimex Co., Ltd, Tokyo, Japan). Next, the NDa dispersion was centrifuged to remove the ND insoluble in water. The resulting supernatant dispersion (NDa-ori) was used in an additional experiment. One milliliter of the NDa-ori dispersion (ND concentration=30 mg ml$^{-1}$), 10 mg of a carboxyl-terminated alkyl chain (sodium (NaOc (C8)), sodium laurate (NaLA (C12)), or sodium oleate (NaOle (C18)), each purchased from FUJIFILM Wako Pure Chemical), and 10 mg of WSC were dissolved in 9 ml of an MES buffer solution (pH 6.0, 100 mM) by sonicating for 5 minutes using a bus-type sonicator (output: 80 W, oscillation frequency: 40 kHz) (USD-2 R; AS ONE, Osaka, Japan). The mixture was additionally stirred vigorously with a stirrer for 1.5 hours at room temperature, and then washed three times with Mill-Q water using centrifugation, and an unreacted material was thus removed. Pellets obtained by centrifugation were re-dispersed in 10 ml of Mill-Q water by irradiating with ultrasonic waves for 10 minutes using a pulsed sonicator. Three types of aminated nanodiamond superparticle (NDa-SP) dispersions were obtained, namely, NaOc(C8)-NDa-SP, NaLA(C12)-NDa-SP, and NaOle(C18)-NDa-SP, and each of these dispersions formed nanoclusters (FIGS. 6(c), (d)).

Figure 7:
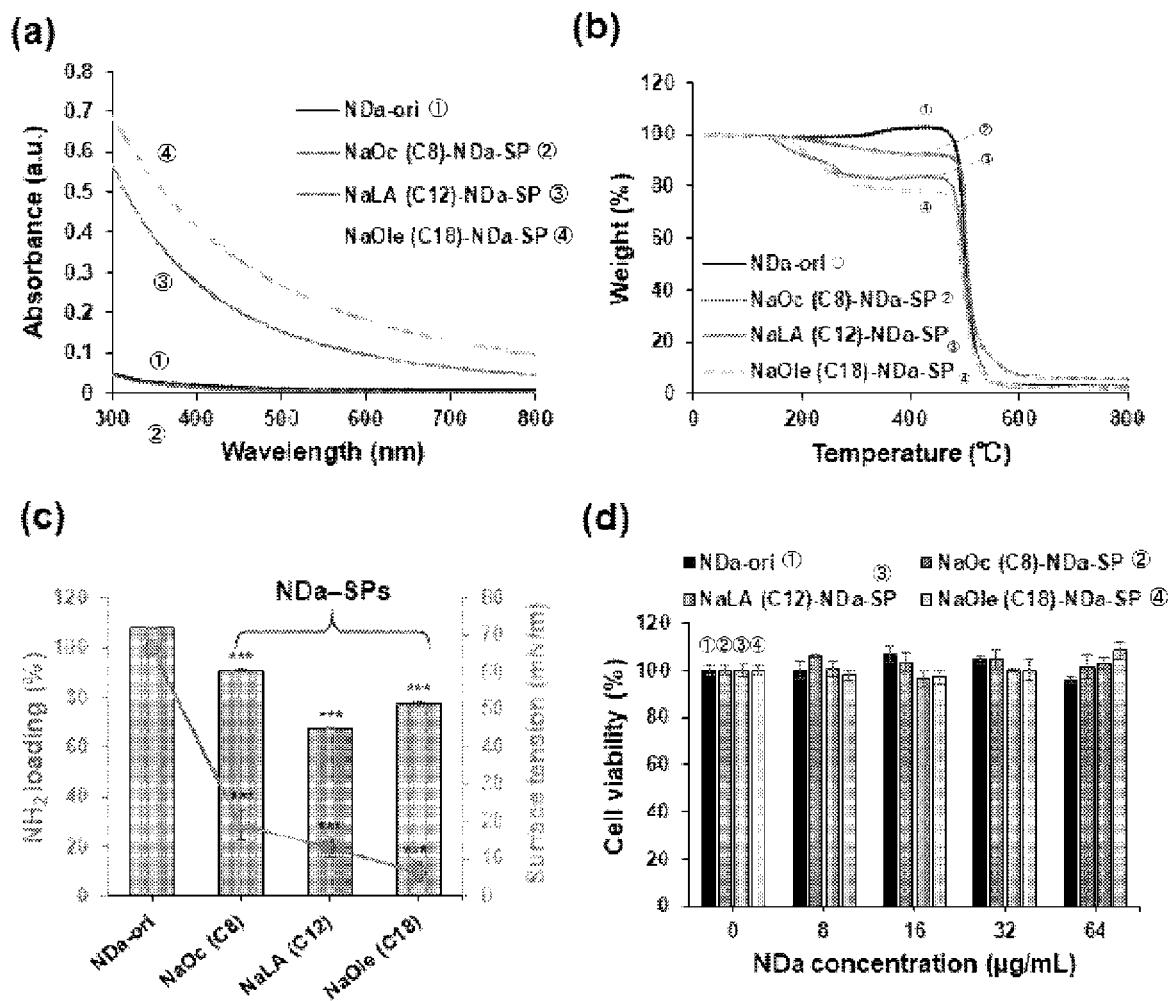
FIG. 7(a) illustrates UV-Vis-NIR absorption spectra of NDa-ori and various NDa-SPs (NaOc(C8)-NDa-SP, NaLA(C12)-NDa-SP, and NaOle(C18)-NDa-SP). The ND concentration in each aqueous solution is 30 μg ml$^{-1}$.
FIG. 7(b) illustrates TGA measurements of the NDa-ori and various NDa-SPs (NaOc(C8)-NDa-SP, NaLA(C12)-NDa-SP, and NaOle(C18)-NDa-SP). It was found that the approximate percentages of NaOc (C8), NaLA (C12), and NaOle (C18) in the NDa-SPs were 8% w/w, 17% w/w, and 24% w/w, respectively.
FIG. 7(c) shows the amount of amino groups ($NH_2$ loading) in the NDa-ori and various NDa-SPs, and the interfacial surface tension. The amount of amino groups was quantitatively determined by using a Kaiser test and calculating the amount of amino groups in each nanoparticle with NDa-ori set to 100%. The surface tension was obtained by measuring samples with an ND concentration of 3 mg ml$^{-1}$ at a water temperature of 25° C. It is clear that the introduction of the alkyl chain reduces the amount of amino groups in the NDa-SPs. In addition, a decrease in surface tension was observed in all of the NDa-SPs as compared to the NDa-ori. This result means that the NDa-SP have a surfactant-like property through alkyl chain introduction.
FIG. 7(d) is a graph showing an evaluation of the cytotoxicity of various NDa-SPs. In this test, cell viability after exposure of various nanoparticles for 24 hours was measured through WST-8 using U2OS cells. The results indicated that all of the NDa-SPs (NaOc(C8)-NDa-SP, NaLA(C12)-NDa-SP, and NaOle(C18)-NDa-SP) exhibited low cytotoxicity.

The NDa-SP dispersions were used in a subsequent experiment. Also, the ND concentration (up to 3 mg ml$^{-1}$) in the NDa-SP dispersion was measured using a UV-Vis-NIR spectrophotometer (FIG. 7(a)). Further, the content amounts of NaOc (C8) (up to 8%, w/w), NaLA (C12) (up to 17%, w/w) and NaOle (C18) (up to 24%, w/w) in the NDa-SP were estimated through thermogravimetric analysis (TGA) (using the Q500 thermogravimetric analyzer; TA Instruments, New Castle, DE, USA).

The amount of amino groups on the ND surface was quantitatively determined using a Kaiser test kit (60017-1EA; Sigma-Aldrich) according to a previously reported method (Yue Yu et al., Nanoscale 10, 8969-8978 (2018).) (FIG. 7(c)).

The surface tensions of the various types of NDa-SP were measured by Mitsui Chemical Analysis & Consulting Service, Inc. (Tokyo, Japan) using a surface tensiometer (CBVP-Z; Kyowa Interface Science Co.) (FIG. 7(c)).

Figure 8:
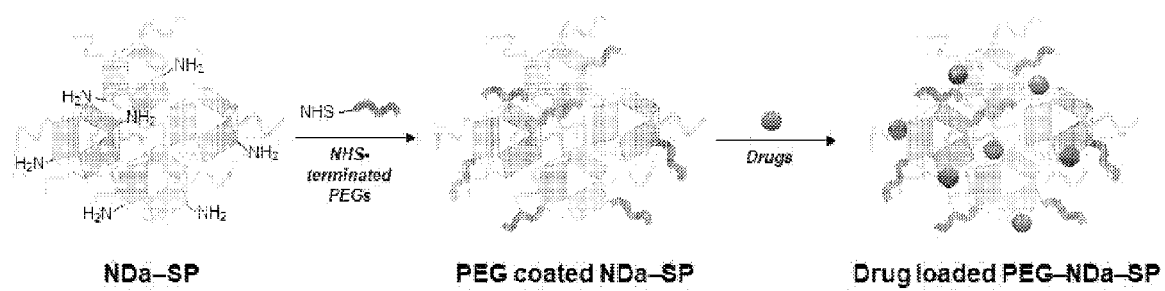
FIG. 8 outlines the synthesis of NDa-SP coated with polyethylene glycol (PEG)(PEG coated-NDa-SP or PEG-NDa-SP) and the encapsulation of a drug in the PEG-NDa-SP using non-covalent bonding. NaOle(C18)-NDa-SP (average particle diameter of 167 nm) with a large particle diameter was not used for PEG modification in this research. The reason for this is that the particle diameter is optimally 100 nm or less to express the enhanced permeability and retention (EPR) effect of nanoparticles, and NaOle(C18)-NDa-SP with a particle diameter of 100 nm or greater was considered to be not suitable for the experiment.
Figure 9:
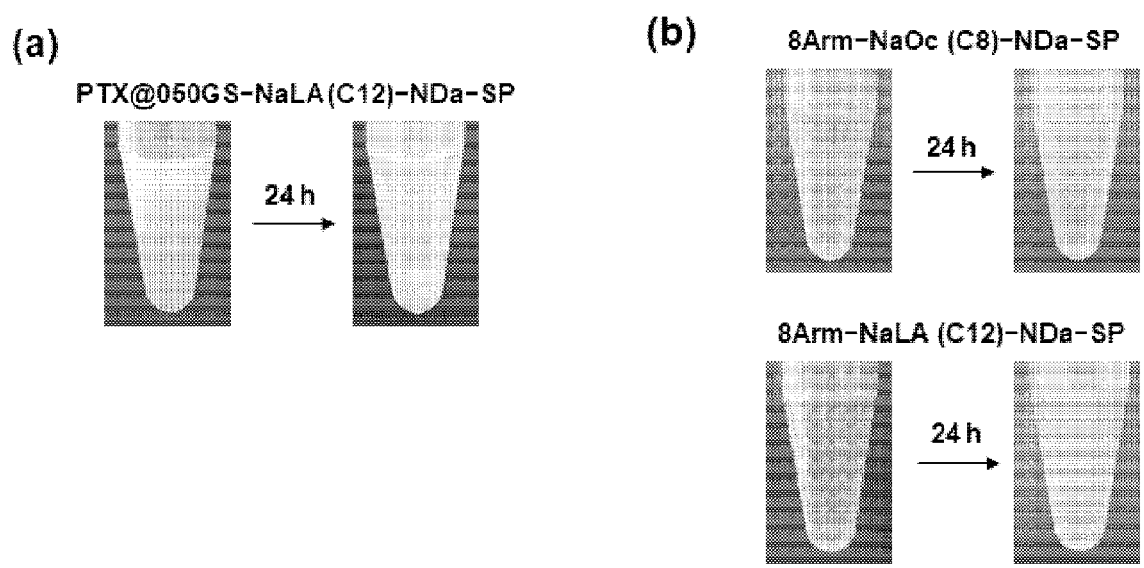
FIG. 9(a) presents a photograph immediately after synthesis of 050GS-NaLA(C12)-NDa-SP into which paclitaxel (PTX) was introduced, and a photograph taken 24 hours later. The concentrations of ND and PTX in the nanocomplexes were 0.3 and 0.1 mg ml$^{-1}$, respectively. After 24 hours, precipitates were formed, and the dispersion stability was not so high, and therefore 050GS-NaLA(C12)-NDa-SP was not used in the following experiments. Note that 050GS indicates that PEG was introduced using the commercially available product Sunbright (trade name) ME-050GS.
FIG. 9(b) presents photographs of 8Arm-NaOc(C8)-NDa-SP and 8Arm-NaLA(C12)-NDa-SP immediately after synthesis and 24 hours later. Both nanocomplexes use NDa-SP having an ND concentration of 3 mg ml$^{-1}$. The dispersibility of the NDa-SP can be improved by using 8Arm. However, since the 8Arm-NaOc(C8)-NDa-SP of the final product is overly dispersible, the concentration of nanoparticles that can be collected by centrifugation is low. From the results above, in the subsequent tests, 8Arm-NaLA(C12)-NDa-SP was used in the experiments. Note that 8-Arm indicates that a PEG group was introduced into the NDa by 8-ArmPEG-SCM, which is a commercially available product.
Figure 10:
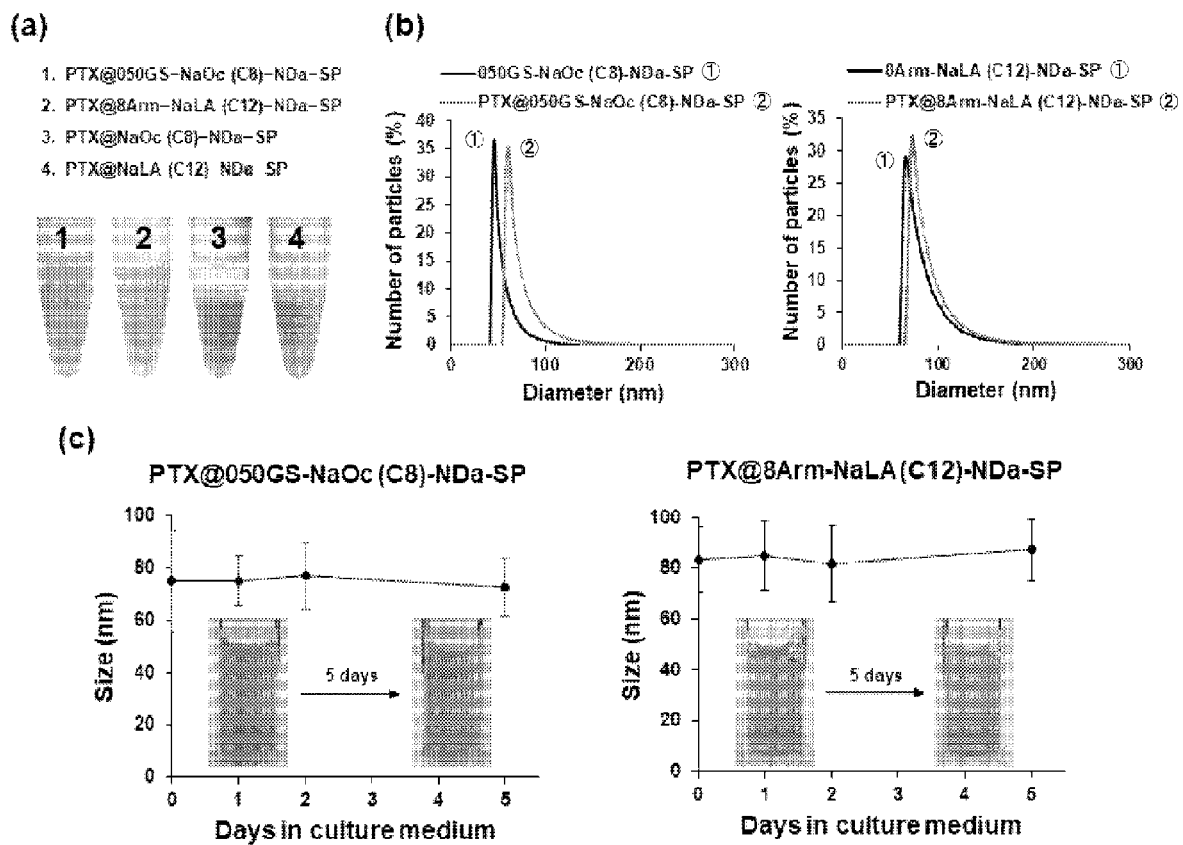
FIG. 10(a) illustrates the dispersibility in water after 24 hours of PEG-modified NDa-SPs (050GS-NaOc(C8)-NDa-SP and 8Arm-NaLA(C12)-NDa-SP) into which PTX was introduced and of PEG-unmodified NDa-SPs (NaOc(C8)-NDa-SP and NaLA(C12)-NDa-SP). The concentrations of NDa and PTX in the nanocomplexes were 3 mg ml$^{-1}$ and 1 mg ml$^{-1}$, respectively. It was found that NDa-SP coated with 050GS and 8Arm exhibits high dispersibility in water even after PTX introduction. From the results of dispersibility in water after drug introduction as described above, it was decided to use 050GS-NaOc(C8)-NDa-SP and 8Arm-NaLa(C12)-NDa-SP as drug carriers for subsequent experiments in this research.
FIG. 10(b) illustrates the change in the average particle diameter of the PEG-NDa-SP before and after PTX introduction.
FIG. 10(c) illustrates evaluations of dispersion stability in water over 5 days of PEG-NDa-SPs (050GS-NaOc(C8)-NDa-SP and 8Arm-NaLA(C12)-NDa-SP) into which PTX was introduced. The data shows chronological DLS measurements (particle diameter) of PTX@050GS-NaOc(C8)-NDa-SP (left) and a PTX@8Arm-NaLA(C12)-NDa-SP aqueous solution (right). The photographs within the graphs show conditions immediately after synthesis and 5 days later. It is clear that no aggregates are visible.
Figure 11:
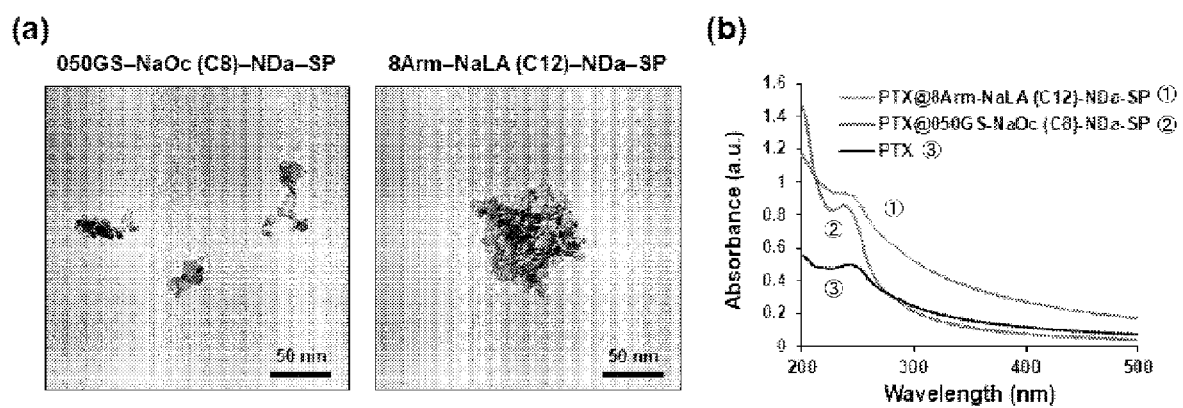
FIG. 11(a) is TEM images of 050GS-NaOc(C8)-NDa-SP and 8Arm-NaLA(C12)-NDa-SP.
FIG. 11(b) is a graph of UV-Vis-NIR absorption spectra of PTX@050GS-NaOc(C8)-NDa-SP, PTX@8Arm-NaLA(C12)-NDa-SP, and PTX. A peak originating from PTX can be confirmed in each nanocomplex, and therefore it was confirmed that PTX was successfully encapsulated as in the concept diagram.
Figure 12:
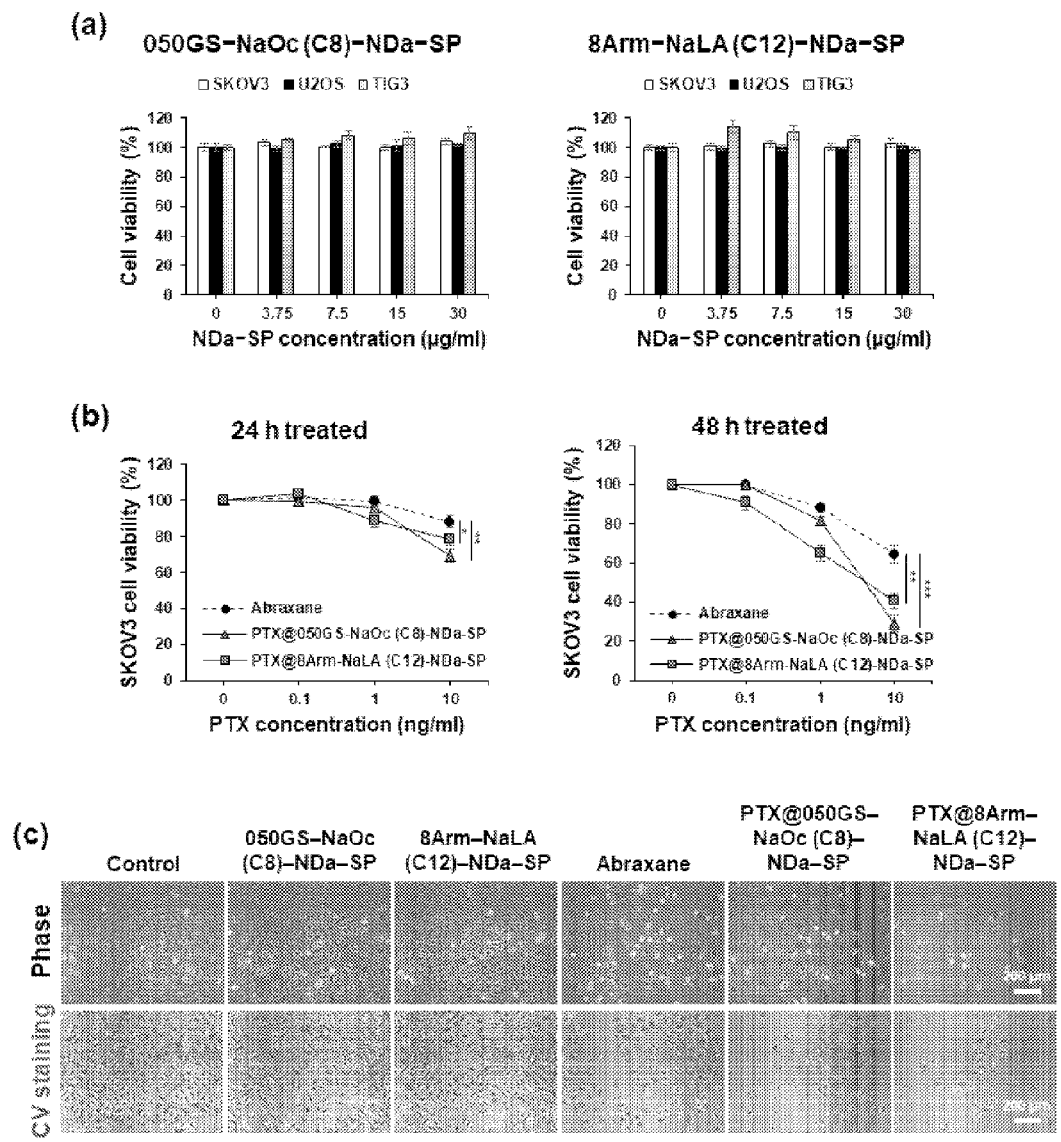
FIG. 12 presents an evaluation of the anti-cancer activity of PEG-NDa-SP into which PTX was introduced.

PEG-modified NDa-SP (PEG-NDa-SP) was synthesized by the following method (FIG. 8). One milliliter of an MES buffer solution (pH 6.0, 500 mM) was added to 10 ml of an NaOc(C8)-NDa-SP aqueous solution or 10 ml of NaLA (C12)-NDa-SP. The mixture was centrifuged (15000 rpm, 10 minutes), and the transparent supernatant solution was carefully removed. Next, 5 mL of DMSO (FUJIFILM Wako Pure Chemical) containing 20 mg of α-succinimidyloxyglutaryl-ω-methoxy, polyoxyethylene (SUNBRIGHT ME-050GS; Yuka Sangyo, Tokyo, Japan) (050GS) or 20 mg of hexaglycerol octa(succinimidyloxyglutaryl)polyoxyethylene (8-Arm PEG-SCM; Funakoshi, Tokyo, Japan) (8Arm) was added to the pellets after centrifugation. The mixture was subjected to sonication for 30 minutes, and then stirred vigorously at room temperature overnight. Lastly, 1 ml of an MES buffer solution (pH 6.0, 100 mM) was added to the reaction solution, and the mixture was washed three times using Milli-Q water and centrifugation. The resulting pellets were re-dispersed in 10 ml of Milli-Q water by irradiating with pulsed ultrasonic waves for 10 minutes. The synthesized 050GS-coated NaOc(C8)-NDa-SP (050GS-NaOc (C8)-NDa-SP) aqueous solution (ND concentration: up to 3 mg ml$^{-1}$) and 8Arm-coated NaLA(C12)-NDa-SP (8Arm-NaLA(C12)-NDa-SP) (ND concentration: up to 3 mg ml$^{-1}$) were used in subsequent experiments. These aqueous solutions formed nanoclusters (FIGS. 10(b), 11(a), 11(b)).

PTX@050GS-NaOc(C8)-NDa-SP and PTX@8Arm-NaLA(C12)-NDa-SP complexes were prepared by the following method. Ten milliliters of Milli-Q water containing 10 mg of paclitaxel (PTX) (FUJIFILM Wako Pure Chemical) were added to pellets of 050GS-NaOc(C8)-NDa-SP or 8Arm-NaLA(C12)-NDa-SP washed by centrifugation, and then the mixture was irradiated for 10 min with pulsed ultrasonic waves. The resulting mixture was stored at 4° C. until just before use. Abraxane was purchased from Taiho Pharmaceutical Co., Ltd. and used as is in an experiment without carrying out a treatment such as chemical modification. These formed nanoclusters (FIGS. 10(b), 11(a), 11(b)).

3. Physical Property Analysis of ND-SP

The structure and morphology of the synthesized ND-SP were analyzed using a high-resolution transmission electron microscope (TEM) (acceleration voltage: 120 kV) (EM-002B; Topcon, Tokyo, Japan) (FIGS. 2(c), 6(c), 6(d), 11(a)).

The particle diameter (hydrodynamic diameter) of the ND-SP was determined by dynamic light scattering (DLS) (using the Photal FPAR-1000; Otsuka Electronics, Osaka, Japan) (FIGS. 2(b), 6(b), 10(b)).

The ND-SP were subjected to spectroscopic analysis, and the concentrations of ND, CPT, and PTX in the ND-SP complexes were estimated using an ultraviolet-visible-near infrared spectrometer (V-730 BIO; Jasco, Tokyo, Japan) (FIGS. 2(a), 3(a), 4(b), 6(a), 7(a), 7(b), 9(a), 9(b), 10(a), 10(c), and 11(b)).

4. Cell Culturing and Cytotoxicity Evaluation

Human osteosarcoma cells (U2OS), human ovarian adenoma cells (SKOV3), and human normal diploid fibroblasts (TIG3) were obtained from the Japanese Collection of Research Bioresources Cell Bank (Tokyo, Japan), and were cultured with Dulbecco's Modified Eagle's Medium (DMEM) (Gibco, Grand Island, NY, USA) containing 10% fetal bovine serum, 2 mM L-glutamine, 1 mM sodium pyruvate, gentamycin, penicillin-streptomycin (100 IU ml$^{-1}$), and Hank's balanced salt solution (Life Technologies, Carlsbad, CA, USA). The cells were cultured in a humidified chamber at 37° C. with a 5% CO2 atmosphere.

Cell viability was evaluated using crystal violet staining (FUJIFILM Wako Pure Chemical) and the Cell Counting Kit (CCK)-8 (Dojindo Laboratories, Kumamoto, Japan) according to the manual thereof. The cells were seeded onto a 96-well plate ($5\times10^3$ cells well$^{-1}$) and incubated overnight. Next, the cells were exposed to a drug or nanocomplex dispersion solution and washed with a fresh culture solution, and then incubated in a CCK-8 solution. Lastly, the percentage of surviving cells was calculated by measuring the absorbance of 450 nm light on a microplate reader (Infinite M200 PRO; Tecan, Mannedorf, Switzerland) (FIGS. 4(a), 4(c), 4(d), 7(d), 12(a), 12(b), 12(c)).

5. Blood Tests

A complete blood count (CBC) and biochemical parameters were measured by Japan SLC and Oriental Yeast Co. (Tokyo, Japan). Specifically, 200 μl of various samples [sterilized water containing ND-SP (NDc-SP: 1.12 mg kg$^{-1}$; NDa-SP: 30 mg kg$^{-1}$), a PBS buffer solution, or sterilized water] were administered through the caudal vein to 10-week old female BALB/cSlc mice (n=5, average weight=21 g; Japan SLC). Blood samples were drawn four weeks after administration of the nanocomplex (Tables 1 to 4).

6. Statistical Analysis of Data

In the data, ± indicates the standard deviation, and n denotes the number of samples that were used. The Student's t-test method was used for statistical analysis of data. The symbols *, , and * indicate p values of <0.05, <0.005, and <0.001, respectively.

TABLE 1

Blood Test Results of Mice Four Weeks After Injection with PBS or Dod(C12)-NDc-SP

| Entry | Unit | PBS (n = 5) | Dod(C12)-NDc-SP (n = 5) | p value |
|---|---|---|---|---|
| WBC | $\times10^2/\mu L$ | 85.3 ± 13.4 | 92.0 ± 16.7 | >0.05 |
| RBC | $\times10^4/\mu L$ | 923.8 ± 21.9 | 938.4 ± 49.7 | >0.05 |
| HGB | g/dl | 13.9 ± 0.6 | 14.3 ± 0.8 | >0.05 |
| HCT | % | 41.4 ± 1.9 | 43.0 ± 2.5 | >0.05 |
| MCV | fl | 45.7 ± 0.5 | 45.9 ± 0.5 | >0.05 |
| MCH | pg | 15.3 ± 0.2 | 15.2 ± 0.1 | >0.05 |
| MCHC | g/dl | 33.5 ± 0.6 | 33.2 ± 0.5 | >0.05 |
| PLT | $\times10^4/\mu L$ | 64.5 ± 11.0 | 70.1 ± 2.7 | >0.05 |

TABLE 2

Biochemical Test Results of Mice Four Weeks After Injection with PBS or Dod(C12)-NDc-SP

| Entry | Unit | PBS (n = 5) | Dod(C12)-NDc-SP (n = 5) | p value |
|---|---|---|---|---|
| CRP | μg/mL | 1.2 ± 0.2 | 0.9 ± 0.2 | >0.05 |
| TP | g/dL | 3.9 ± 0.2 | 4.1 ± 0.1 | >0.05 |
| ALB | g/dL | 2.6 ± 0.2 | 2.8 ± 0.0 | >0.05 |
| BUN | mg/dL | 21.6 ± 0.6 | 23.5 ± 3.1 | >0.05 |
| CRE | mg/dL | 0.13 ± 0.02 | 0.12 ± 0.01 | >0.05 |
| Na | mEq/L | 145.6 ± 1.4 | 148.6 ± 0.5 | >0.05 |
| K | mEq/L | 3.9 ± 0.4 | 3.4 ± 0.2 | >0.05 |
| Cl | mEq/L | 113.6 ± 1.0 | 117.0 ± 0.9 | >0.05 |
| AST | IU/L | 59.4 ± 11.0 | 70.5 ± 11.0 | >0.05 |
| ALT | IU/L | 31.2 ± 5.0 | 39.0 ± 7.2 | >0.05 |
| LDH | IU/L | 230.0 ± 41.0 | 272.5 ± 44.8 | >0.05 |
| AMY | IU/L | 1597.0 ± 133.9 | 1624.2 ± 75.7 | >0.05 |
| CK | IU/L | 158.8 ± 45.4 | 166.4 ± 59.1 | >0.05 |

Abbreviations:
WBC, white blood cell;
RBC, red blood cell;
HGB, hemoglobin;
HCT, hematocrit;
MCV, mean cell volume;
MCH, mean cell hemoglobin;
MCHC, mean cell hemoglobin concentration;
PLT, platelet;
CRP, C-reactive protein;
TP, total protein;
ALB, albumin;
BUN, blood urea nitrogen;
CRE creatinine;
AST, aspartate aminotransferase;
ALT, alanine transferase;
LDH, lactate dehydrogenase;
AMY, amylase;
CK, creatine kinase When the complete blood count (CBC) and biochemical parameters four weeks after administration of the Dod(C12)-NDc-SP dispersion or PBS into the caudal vein of the mice were examined, a significant difference between the samples was not found. This result means that the Dod(C12)-NDc-SP is highly biocompatible.

TABLE 3

Blood Test Results of Mice Four Weeks After Injection with PBS or PEG-NDa-SP

| Entry | Unit | Sterilized water (n = 5) | 050GS-NaOc(C8)-NDa-SP (n = 5) | 8Arm-NaLA(C12)-NDa-SP (n = 5) | p value vs water |
|---|---|---|---|---|---|
| WBC | $\times10^2/\mu L$ | 59.0 ± 10.7 | 61.0 ± 4.8 | 59.6 ± 12.0 | >0.05 |
| RBC | $\times10^4/\mu L$ | 916.8 ± 11.7 | 890.8 ± 21.3 | 901.4 ± 7.1 | >0.05 |
| HGB | g/dl | 14.5 ± 0.2 | 14.0 ± 0.4 | 14.1 ± 0.2 | >0.05 |
| HCT | % | 42.8 ± 0.5 | 41.5 ± 0.9 | 41.8 ± 0.4 | >0.05 |
| MCV | fl | 46.7 ± 0.3 | 46.6 ± 0.2 | 46.3 ± 0.4 | >0.05 |
| MCH | pg | 15.8 ± 0.1 | 15.7 ± 0.1 | 15.7 ± 0.1 | >0.05 |
| MCHC | g/dl | 33.9 ± 0.3 | 33.7 ± 0.2 | 33.8 ± 0.3 | >0.05 |
| PLT | $\times10^4/\mu L$ | 59.5 ± 4.8 | 64.1 ± 5.2 | 58.2 ± 1.9 | >0.05 |

TABLE 4

Biochemical Test Results of Mice Four Weeks After Injection with PBS or PEG-NDa-SP

| Entry | Unit | Sterilized water (n = 5) | 050GS-NaOc(C8)-NDa-SP (n = 5) | 8Arm-NaLA(C12)-NDa-SP (n = 5) | p value vs water |
|---|---|---|---|---|---|
| CRP | µg/mL | 1.2 ± 0.2 | 1.0 ± 0.1 | 1.1 ± 0.1 | >0.05 |
| TP | g/dL | 4.1 ± 0.3 | 4.1 ± 0.1 | 4.1 ± 0.2 | >0.05 |
| ALB | g/dL | 2.7 ± 0.2 | 2.8 ± 0.1 | 2.8 ± 0.1 | >0.05 |
| BUN | mg/dL | 22.0 ± 4.6 | 23.1 ± 2.6 | 21.7 ± 1.8 | >0.05 |
| CRE | mg/dL | 0.14 ± 0.03 | 0.12 ± 0.01 | 0.11 ± 0.01 | >0.05 |
| Na | mEq/L | 148.2 ± 0.8 | 149.8 ± 1.1 | 150.0 ± 1.1 | >0.05 |
| K | mEq/L | 3.7 ± 0.3 | 3.8 ± 0.1 | 3.5 ± 0.2 | >0.05 |
| Cl | mEq/L | 112.2 ± 1.0 | 113.0 ± 1.4 | 115.0 ± 0.9 | >0.05 |
| AST | IU/L | 60.8 ± 14.3 | 67.2 ± 14.8 | 64.8 ± 6.4 | >0.05 |
| ALT | IU/L | 40.0 ± 13.0 | 39.0 ± 7.3 | 36.6 ± 7.0 | >0.05 |
| LDH | IU/L | 266.2 ± 90.1 | 296.2 ± 38.6 | 265.4 ± 51.4 | >0.05 |
| AMY | IU/L | 1852.4 ± 181.2 | 1683.4 ± 95.5 | 1823.8 ± 74.3 | >0.05 |
| CK | IU/L | 232.2 ± 63.2 | 219.2 ± 68.4 | 202.0 ± 55.6 | >0.05 |

Abbreviations:
WBC, white blood cell;
RBC, red blood cell;
HGB, hemoglobin;
HCT, hematocrit;
MCV, mean cell volume;
MCH, mean cell hemoglobin;
MCHC, mean cell hemoglobin concentration;
PLT, platelet;
CRP, C-reactive protein;
TP, total protein;
ALB, albumin;
BUN, blood urea nitrogen;
CRE creatinine;
AST, aspartate aminotransferase;
ALT, alanine transferase;
LDH, lactate dehydrogenase;
AMY, amylase;
CK, creatine kinase When the complete blood count (CBC) and biochemical parameters were examined four weeks after administration into the caudal vein of mice of only sterile water or sterile water in which PEG-NDc-SP was dispersed, a significant difference between the samples was not found. This result means that the PEG-NDc-SP is highly biocompatible.

The invention claimed is:

1. A nanocluster in which carbon nanomaterials covalently bonded to a $C_8$-$C_{14}$ alkyl group or a $C_8$-$C_{18}$ alkenyl group, and further covalently bonded to a polyalkylene glycol are self-assembled by non-covalent bonding,
wherein the $C_8$-$C_{14}$ alkyl group or the $C_8$-$C_{18}$ alkenyl group is located within the nanocluster and on a surface of the nanocluster,
wherein the polyalkylene glycol is located on the surface of the nanocluster,
wherein an average particle diameter of primary particles of the carbon nanomaterials covalently bonded to the $C_8$-$C_{14}$ alkyl group or the $C_8$-$C_{18}$ alkenyl group and the polyalkylene glycol is from 1 to 12 nm, and
wherein an average particle diameter of the nanocluster is from 30 to 500 nm.

2. The nanocluster according to claim 1, wherein the $C_8$-$C_{14}$ alkyl group or the $C_8$-$C_{18}$ alkenyl group, and the polyalkylene glycol are covalently bonded to the carbon nanomaterials by any linking group selected from the group consisting of —NH—, —O—, —CO—O—, —O—CO—, —CO—NH—, —NH—CO—, —NH—CO—O—, —O—CO—NH—, —O—CO—O—, and —NH—CO—NH—.

3. The nanocluster according to claim 1, wherein the carbon nanomaterials have at least one surface group selected from the group consisting of OH, COOH, and $NH_2$, and the $C_8$-$C_{14}$ alkyl group or the $C_8$-$C_{18}$ alkenyl group is covalently bonded to the carbon nanomaterials through the surface group.

4. The nanocluster according to claim 1, wherein the carbon nanomaterials have at least one surface group selected from the group consisting of OH, COOH, and $NH_2$, and the polyalkylene glycol is covalently bonded to the carbon nanomaterials through the surface group.

5. The nanocluster according to claim 1, complexed with an active ingredient, wherein the active ingredient is located within the nanocluster and on the surface of the nanocluster.

6. The nanocluster according to claim 5, wherein the active ingredient is a physiologically active substance, a labeling substance, a perfume, an essential oil, or an organic pigment.

7. The nanocluster according to claim 1, wherein the carbon nanomaterials are carbon nanodiamonds or carbon nanodots.

8. The nanocluster according to claim 1, wherein said polyalkylene glycol is polyethylene glycol.

9. The nanocluster according to claim 1, wherein said carbon nanomaterial is a carboxylated or aminated nanodiamond.

10. The nanocluster according to claim 1, wherein the $C_8$-$C_{14}$ alkyl group is an amino-terminated or carboxy-terminated alkyl group.

11. A delivery carrier for an active ingredient, the delivery carrier comprising the nanocluster according to claim 1.

12. A carbon nanomaterial covalently bonded to an amino-terminated or carboxy-terminated $C_8$-$C_{14}$ alkyl group and/or a $C_8$-$C_{18}$ alkenyl group and a polyalkylene glycol.

13. The carbon nanomaterial according to claim 12, wherein the $C_8$-$C_{14}$ alkyl group or the $C_8$-$C_{18}$ alkenyl group and the polyalkylene glycol are covalently bonded by any linking group selected from the group consisting of —NH—, —O—, —CO—O—, —O—CO—, —CO—NH—, —NH—CO—, —NH—CO—O—, —O—CO—NH—, —O—CO—O—, and —NH—CO—NH—.

14. The carbon nanomaterial according to claim 12, wherein the carbon nanomaterial is a carbon nanodiamond.

15. The carbon nanomaterial according to claim 12, wherein said polyalkylene glycol is polyethylene glycol.

16. The carbon nanomaterial according to claim 12, wherein said carbon nanomaterial is a carboxylated or aminated nanodiamond.

17. A pharmaceutical composition comprising the self-assembled nanocluster according to claim 1, the self-assembled nanocluster being complexed with a drug.

\* \* \* \* \*